US009480621B2

(12) United States Patent
Imai

(10) Patent No.: US 9,480,621 B2
(45) Date of Patent: Nov. 1, 2016

(54) MEDICAL INSTRUMENT

(71) Applicant: Terumo Kabushiki Kaisha, Tokyo (JP)

(72) Inventor: Masaomi Imai, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 328 days.

(21) Appl. No.: 14/304,533

(22) Filed: Jun. 13, 2014

(65) Prior Publication Data

US 2014/0291324 A1 Oct. 2, 2014

Related U.S. Application Data

(63) Continuation of application No. PCT/JP2012/080948, filed on Nov. 29, 2012.

(30) Foreign Application Priority Data

Dec. 15, 2011 (JP) ................................ 2011-275000

(51) Int. Cl.
*A61B 19/00* (2006.01)
*A61J 1/14* (2006.01)
*A61J 1/20* (2006.01)

(52) U.S. Cl.
CPC ............ *A61J 1/1412* (2013.01); *A61J 1/1418* (2015.05); *A61J 1/2096* (2013.01); *A61J 1/201* (2015.05); *A61J 1/2044* (2015.05); *A61J 1/2065* (2015.05); *A61J 1/2068* (2015.05)

(58) Field of Classification Search
CPC ...... A61J 1/1412; A61J 1/1418; A61J 1/201; A61J 1/2065
See application file for complete search history.

(56) References Cited

U.S. PATENT DOCUMENTS 6,258,078 B1 7/2001 Thilly
2007/0108205 A1 5/2007 Porras

FOREIGN PATENT DOCUMENTS

| | | |
|---|---|---|
| JP | U-1989-023475 U | 2/1989 |
| JP | U-1989-023475 U1 | 2/1989 |
| JP | 2000-344265 A | 12/2000 |
| JP | 2001-508680 A | 7/2001 |
| WO | WO-2010/089388 A1 | 8/2010 |

OTHER PUBLICATIONS

International Search Report dated Mar. 5, 2013 issued in PCT/JP2012/080948.

*Primary Examiner* — Leslie Deak
(74) *Attorney, Agent, or Firm* — Foley & Lardner LLP

(57) ABSTRACT

A medical instrument configured to cover at least a mouth section of a medical container that includes a container body with the mouth section at a distal end and a sealing member that seals the mouth section, includes: a cap comprising a cylindrical body; an adapter; and a proximal-end side structure body. The medical device is configured such that, when screw-engagement between a second cap-side screw-engaged portion and a proximal-end side screw-engaged portion is released by rotating the cap around a center axis, the adapter moves in the proximal-end direction while being prevented from rotating by a guide portion, thereby allowing an adapter-side screw-engaged portion to be detached from a first cap-side screw-engaged portion, and further allowing a hollow needle to penetrate the sealing member so that an inside of the container body communicates with an outside via the hollow needle.

20 Claims, 12 Drawing Sheets

MEDICAL INSTRUMENT

CROSS-REFERENCE TO RELATED APPLICATIONS

This application is a continuation application filed under 35 U.S.C. 111(a) claiming the benefit under 35 U.S.C. §§120 and 365(c) of PCT International Application No. PCT/JP2012/080948 filed on Nov. 29, 2012, which is based upon and claims the benefit of priority of Japanese Application No. 2011-275000 filed on Dec. 15, 2011, the entire contents of which are hereby incorporated by reference in their entireties.

BACKGROUND

1. Technical Field

The present invention relates to a medical instrument.

2. Background Art

Generally, many medicines are stored in vial containers (medicine-storing containers) having a bottomed tubular shape and having a mouth section at a distal-end portion. The vial container storing a medicine is housed in a storage instrument when the medicine is in an unused state (see, for example, International Publication No. WO 2010/089388 A, (hereinafter "the '388 publication").

The storage instrument disclosed in the '388 publication includes a cover (container) including a member having a bottomed tubular shape and formed in a size capable of storing the vial container, and a cap detachably mounted on a distal-end opening of the cover. The vial container housed inside the storage instrument having the above configuration is used in accordance with following procedure.

First, an unused vial container housed inside the storage instrument, an adapter for connecting a syringe to the mouth section of the vial container, and the syringe in which liquid to dilute or dissolve a medicine is preliminarily filled are prepared.

Next, the cap is detached from the cover. By this detachment, the mouth section of the vial container is exposed from the distal-end opening of the cover.

Then, the adapter is mounted on (attached to) the mouth section of the vial container.

Subsequently, the syringe is connected to the adapter mounted on the mouth section of the vial container, and the syringe is operated to dilute or dissolve the medicine while connected.

Next, the medicine having been diluted or dissolved is sucked to the syringe, and the syringe is detached from the adapter.

Thus, in the case of using the vial container housed in the storage instrument disclosed in the '388 publication, it is necessary to mount the separately prepared adapter on the vial container every time after detaching the cap from the cover. For this reason, adapter mounting is bothersome and the vial container cannot be used immediately after detachment of the cap.

SUMMARY OF THE INVENTION

Technical Problem

One object of certain embodiments of the present invention is to provide a medical instrument in which a medical container can be used immediately after detaching a cap.

In one embodiment, a medical instrument that covers at least a mouth section of a medical container having a tubular shape and including a container body with the mouth section at a distal end thereof and a soft sealing member that seals the mouth section, includes: a cap including a first cap-side screw-engaged portion and a second cap-side screw-engaged portion, the first cap-side screw-engaged portion being formed of a cylindrical body and including a first screw portion formed in a spiral shape on an inner peripheral side of the cylindrical body around a center axis thereof and the second cap-side screw-engaged portion including a second screw portion formed in a spiral shape around the center axis on a more proximal-end side than the first cap-side screw-engaged portion on an outer peripheral side of the cylindrical body or on the inner peripheral side of the cylindrical body; an adapter including an adapter-side screw-engaged portion and a hollow needle that can penetrate the sealing member, the adapter-side screw-engaged portion being arranged movable in a proximal-end direction inside the cap and configured to be screw-engaged with the first cap-side screw-engaged portion; and a proximal-end side structure body including a proximal-end side screw-engaged portion to be screw-engaged with the second cap-side screw-engaged portion, a mounting section to be mounted on the container body so as to cover at least the mouth section, and a guide portion configured to guide the adapter along a moving direction and also restrict the adapter from rotating with the cap when the adapter moves in the proximal-end direction. A pitch at the first screw portion is larger than a pitch at the second screw portion. When screw-engagement between the second cap-side screw-engaged portion and the proximal-end side screw-engaged portion is released by rotating the cap around the center axis and the cap is detached from the proximal-end side structure body, the adapter moves in the proximal-end direction while being prevented from rotating by the guide portion, thereby allowing the adapter-side screw-engaged portion to be detached from the first cap-side screw-engaged portion, and further allowing the hollow needle to penetrate the sealing member so that inside of the container body communicates with outside via the hollow needle.

In one aspect, the number of turns of a screw at the first screw portion is equal to or less than the number of turns of a screw at the second screw portion.

In one aspect, the proximal-end side structure body includes a housing section having a bottomed tubular shape and housing the container body on the proximal-end side of the proximal-end side screw-engaged portion. The proximal-end side structure body is formed of two separate portions: a guide structure body in which the guide portion and the mounting section are integrated; and the outer cover member in which the housing section and the proximal-end side screw-engaged portion are integrated before assembling the cap, the adapter and the proximal-end side structure body. The cap, the adapter and the guide structure body are assembled first and then the outer cover member is assembled at the time of assembling the cap, the adapter and the proximal-end side structure body. The medical instrument includes a rotation restricting unit configured to restrict the guide structure body from rotating with respect to the outer cover member. In a state after completing the assembly of the cap, the adapter and the proximal-end side structure body, rotation of the guide structure body with respect to the outer cover member is restricted by the rotation restricting unit, and the guide structure body can be separated from the cap by rotating the cap around the center axis.

In one aspect, the cap is connected to a cap body positioned at a distal-end side and to a proximal-end side of the cap body, and includes a ring portion and a breaking portion which is breakable in a boundary portion between the cap body and ring portion, and a rotation preventing portion configured to prevent the guide structure body from rotating with respect to the cap body is formed on the ring portion. The second cap-side screw-engaged portion is formed on the outer peripheral side of the cap body and the ring portion. In the assembled state, rotation of the ring portion with respect to the proximal-end side structure body is restricted by the rotation restricting unit, and rotating force generated by rotating the cap around the center axis breaks the breaking portion to separate the cap body from the ring portion.

In one aspect, the medical instrument includes a unit for fixing the ring portion and the guide structure body.

In one aspect, the guide portion is formed of at least one long portion having a long shape along the center axis and can be separated into a distal-end side portion and a proximal-end side portion. When the cap is detached, the distal-end side portion of the long portion stays on the cap body side and the proximal-end side portion stays on the ring portion side.

In one aspect, the rotation restricting unit includes: a restricting section formed on the inner peripheral portion of the housing section in a part different from where the proximal-end side screw-engaged portion is formed, and configured to restrict the container body from rotating around the center axis; a projected portion formed on the outer peripheral portion of the container body in a projecting manner; and an engagement portion formed on the mounting section and to be engaged with the projected portion in a state where the assembly is completed.

In one aspect, the adapter includes a connector configured to communicate with the hollow needle and to be connected to the syringe while the cap is detached.

When the syringe is connected to the connector, the syringe communicates with the container body via the connector and the hollow needle.

According to certain embodiments of the present invention, the adapter is configured to be mounted on the medical container, interlocking with detachment of the cap.

On the other hand, for example, in the storage instrument housing the medical container according to the related art, where the cover having a bottomed tubular shape and the cap detachably mounted on the distal-end opening of the cover are provided, the cap is detached from the cover and the adapter is mounted on the medical container after detachment of the cap.

According to certain embodiments of the present invention, the bothersome operation of mounting the adapter on the medical container after detaching the cap, executed in the storage instrument according to the related art, can be omitted. Therefore, according to certain embodiments of the present invention, the medical container can be used immediately after detaching the cap, thereby achieving excellent operability.

DETAILED DESCRIPTION

Now, a medical instrument according to an embodiment of the present invention will be described with reference to the attached drawings.

Figure 1:
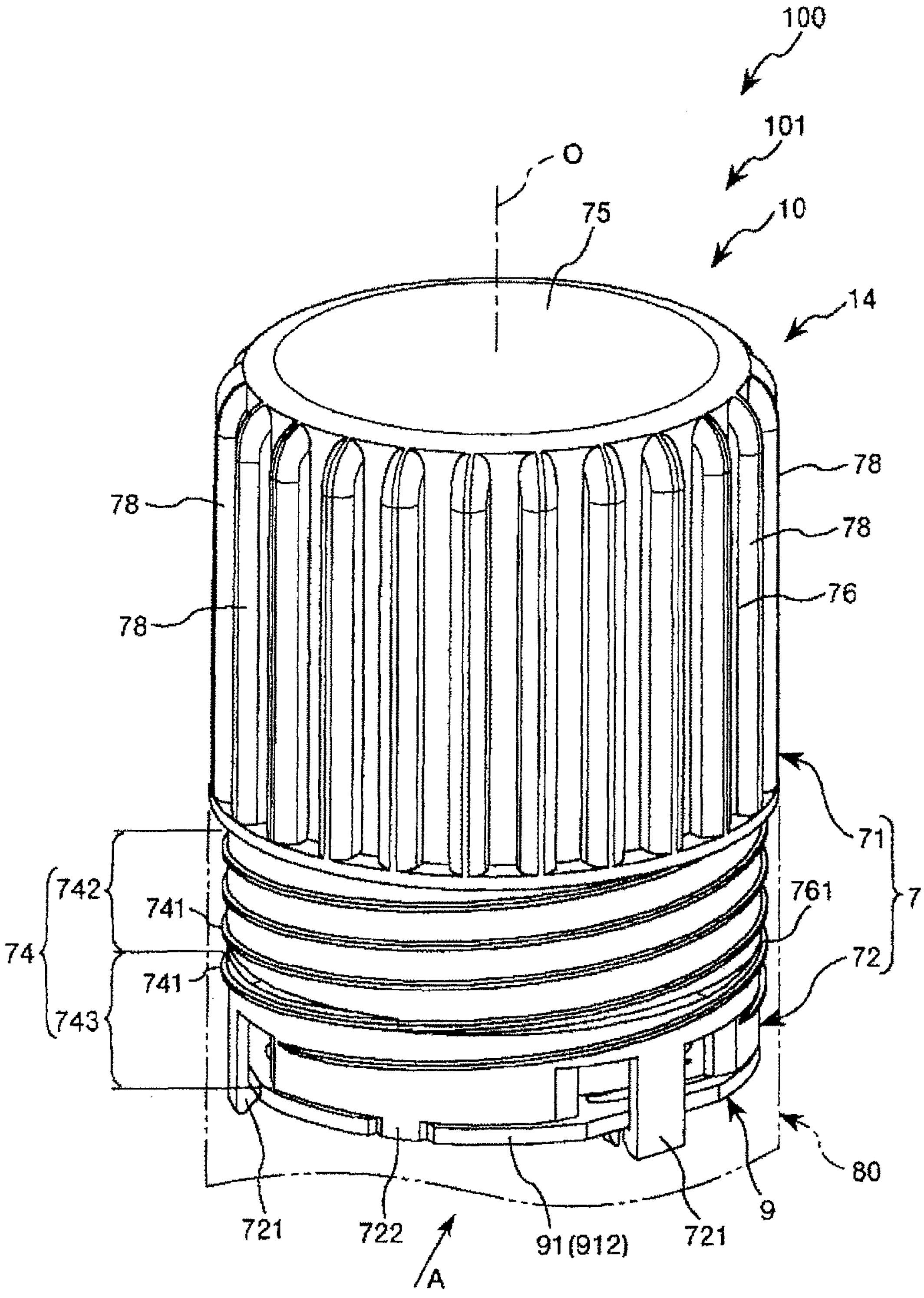
FIG. 1 is perspective view illustrating a medical instrument according to an embodiment of the present invention.
Figure 2:
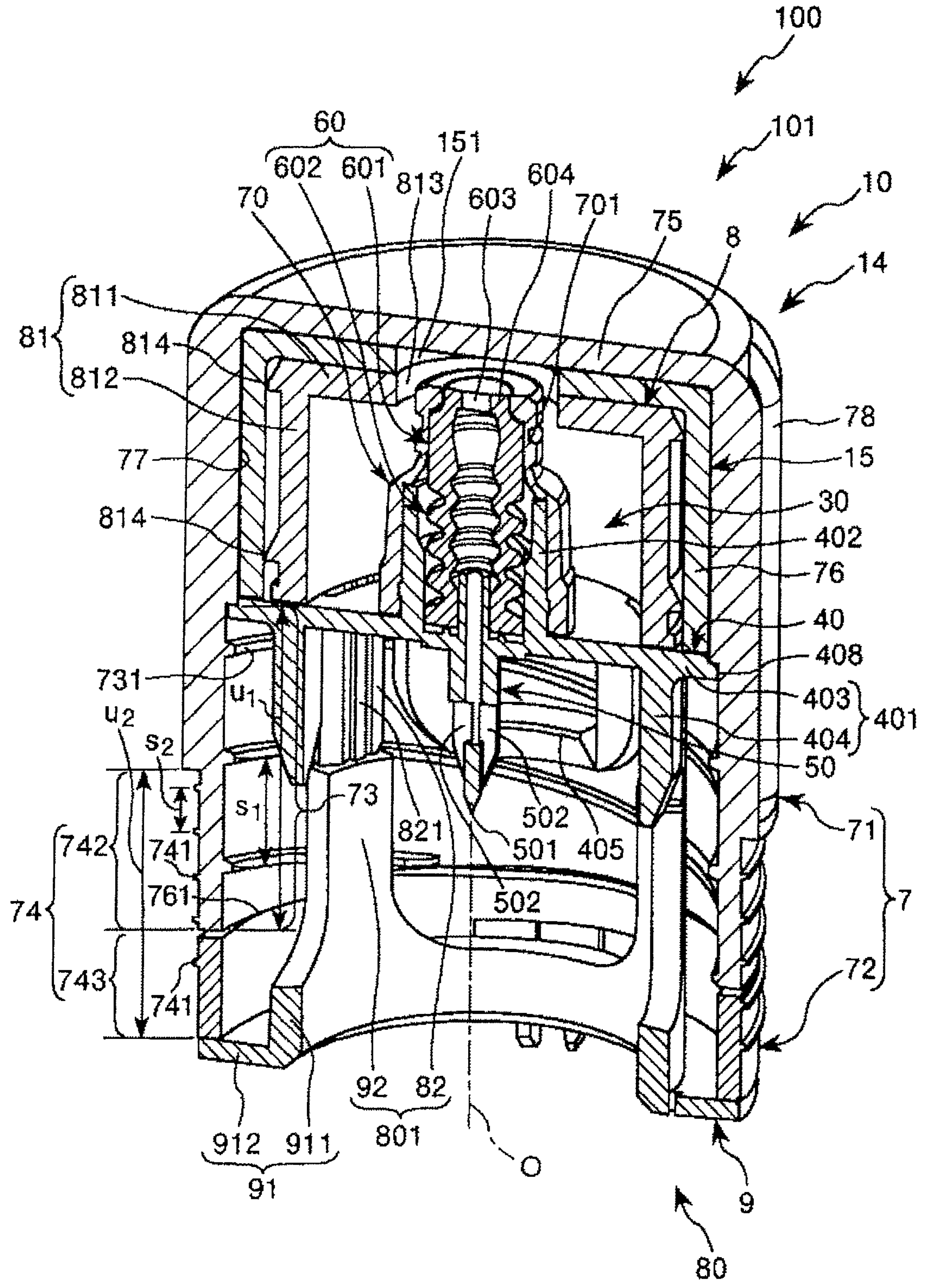
FIG. 2 is a longitudinal sectional perspective view illustrating the medical instrument illustrated in FIG. 1.
Figure 3:
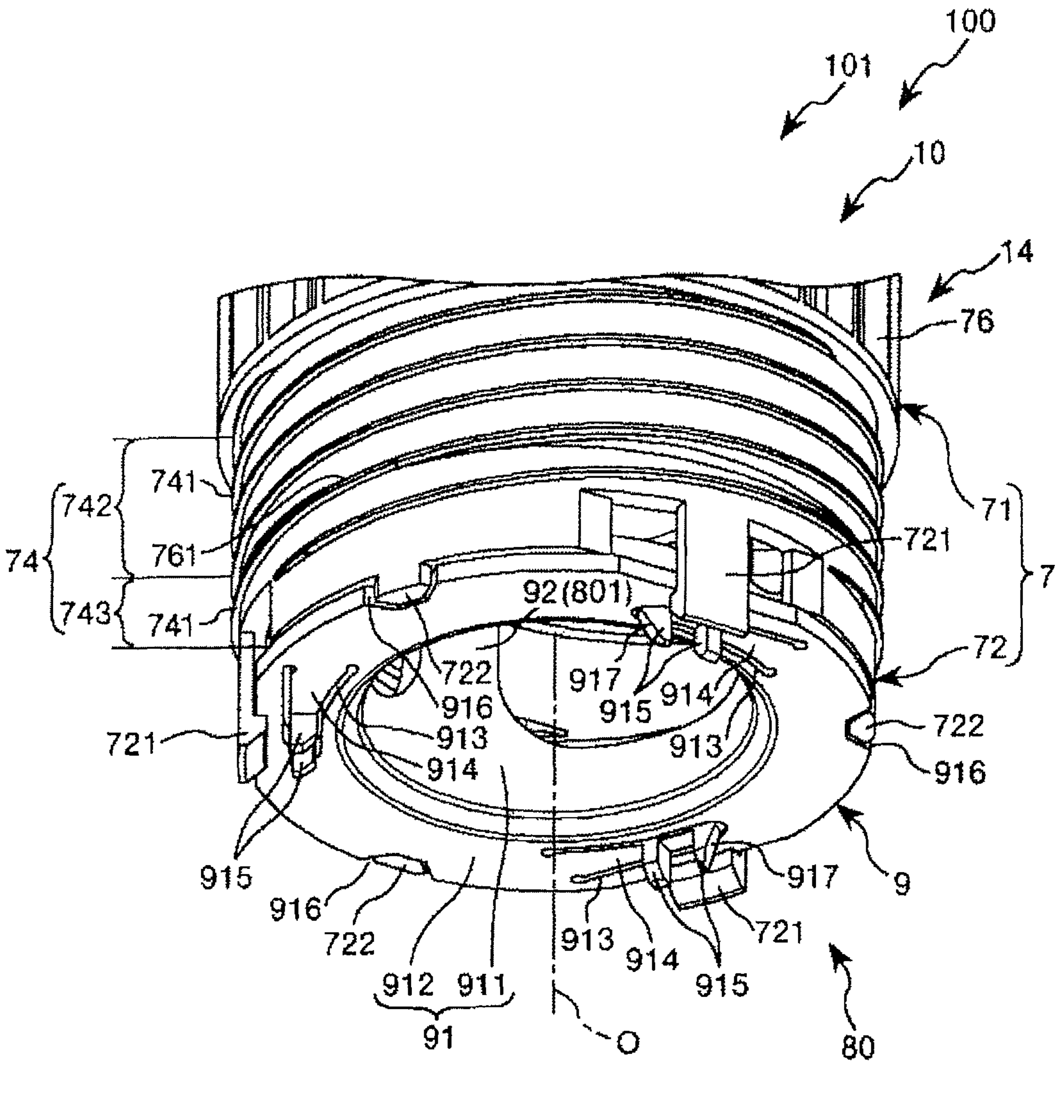
FIG. 3 is a view seen from the direction of an arrow A illustrated in FIG. 1.
Figure 4:
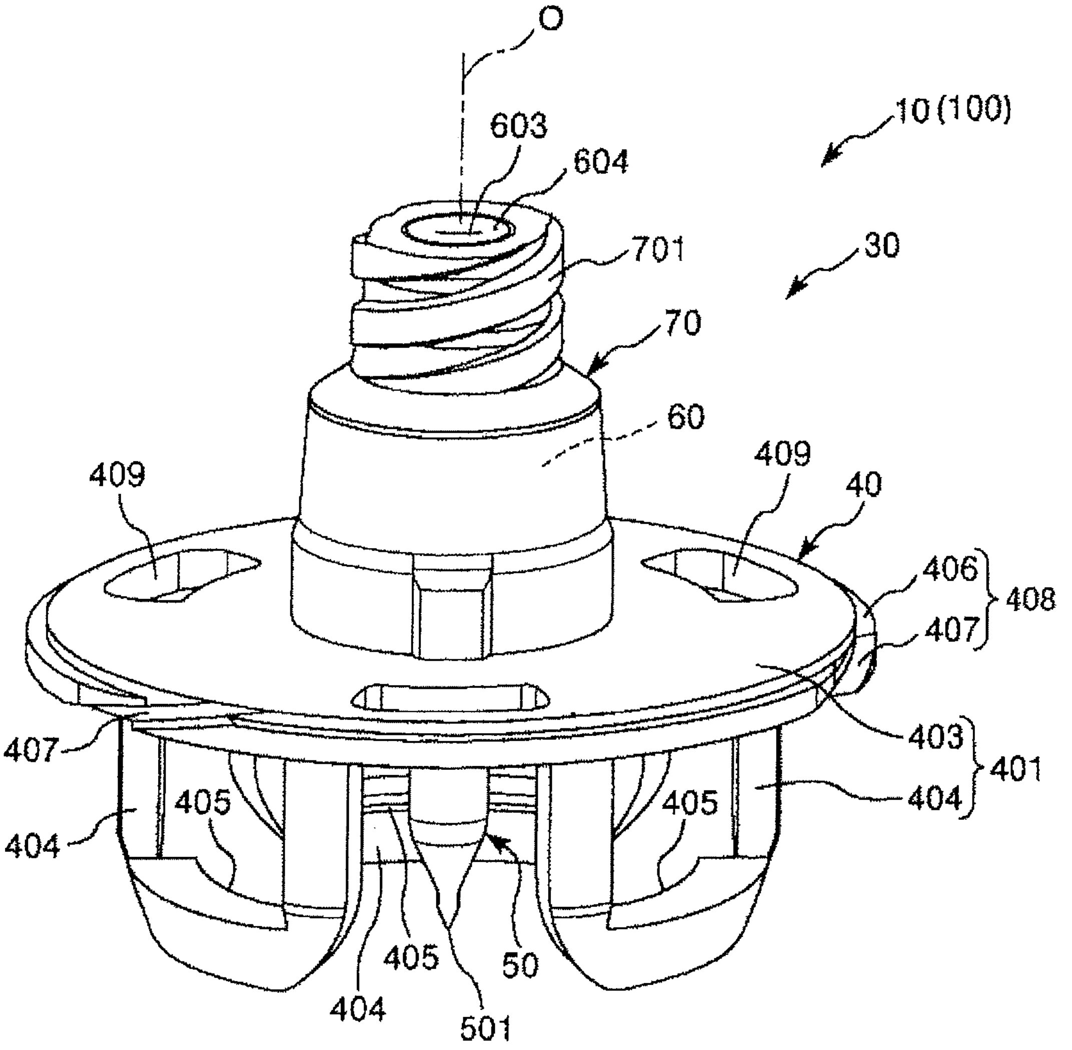
FIG. 4 is a perspective view illustrating an adapter included in the medical instrument according to an embodiment of the present invention.
Figure 5:
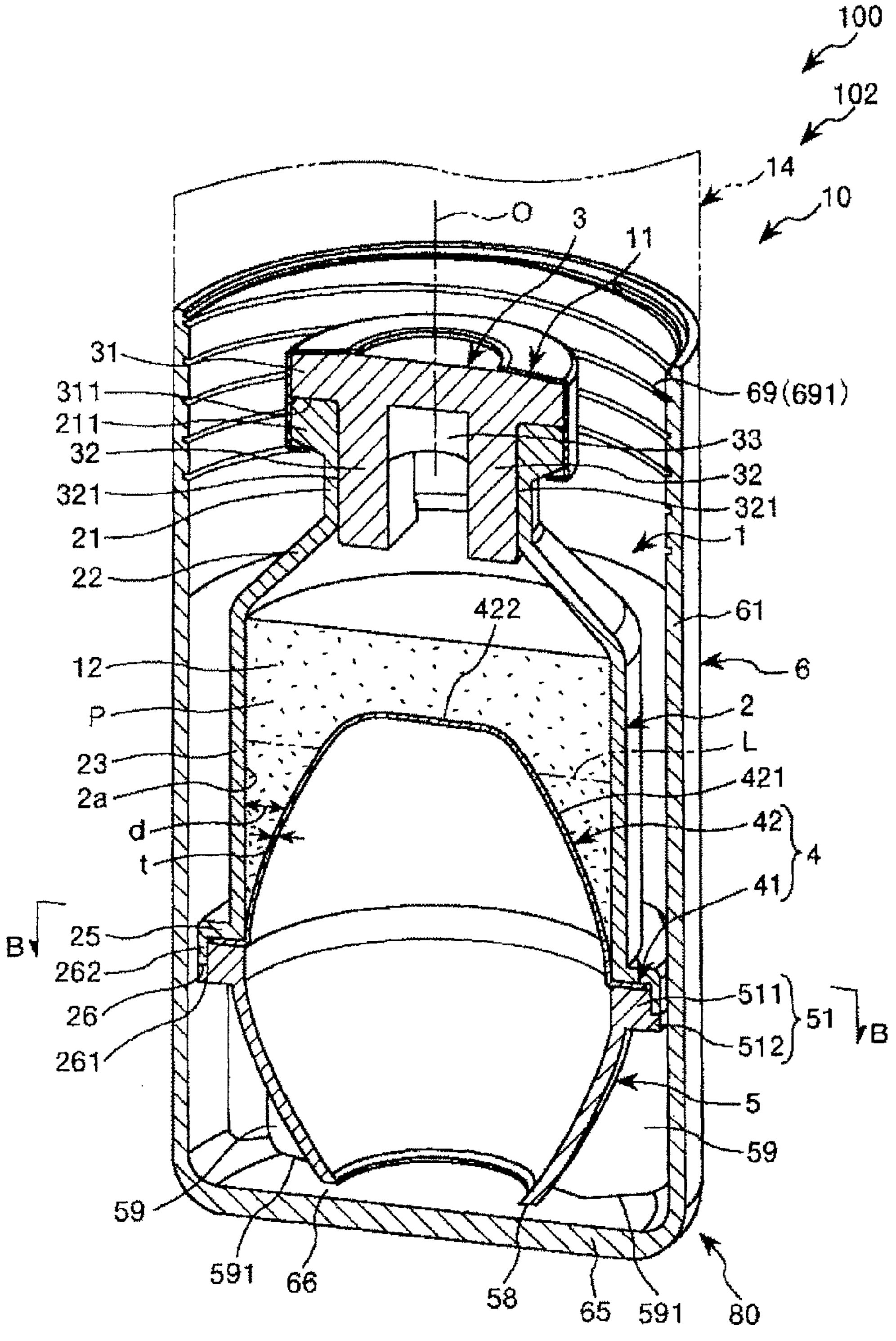
FIG. 5 is a longitudinal sectional perspective view illustrating a state in which the medical container is housed in the medical instrument according to an embodiment of the present invention.
Figure 6:
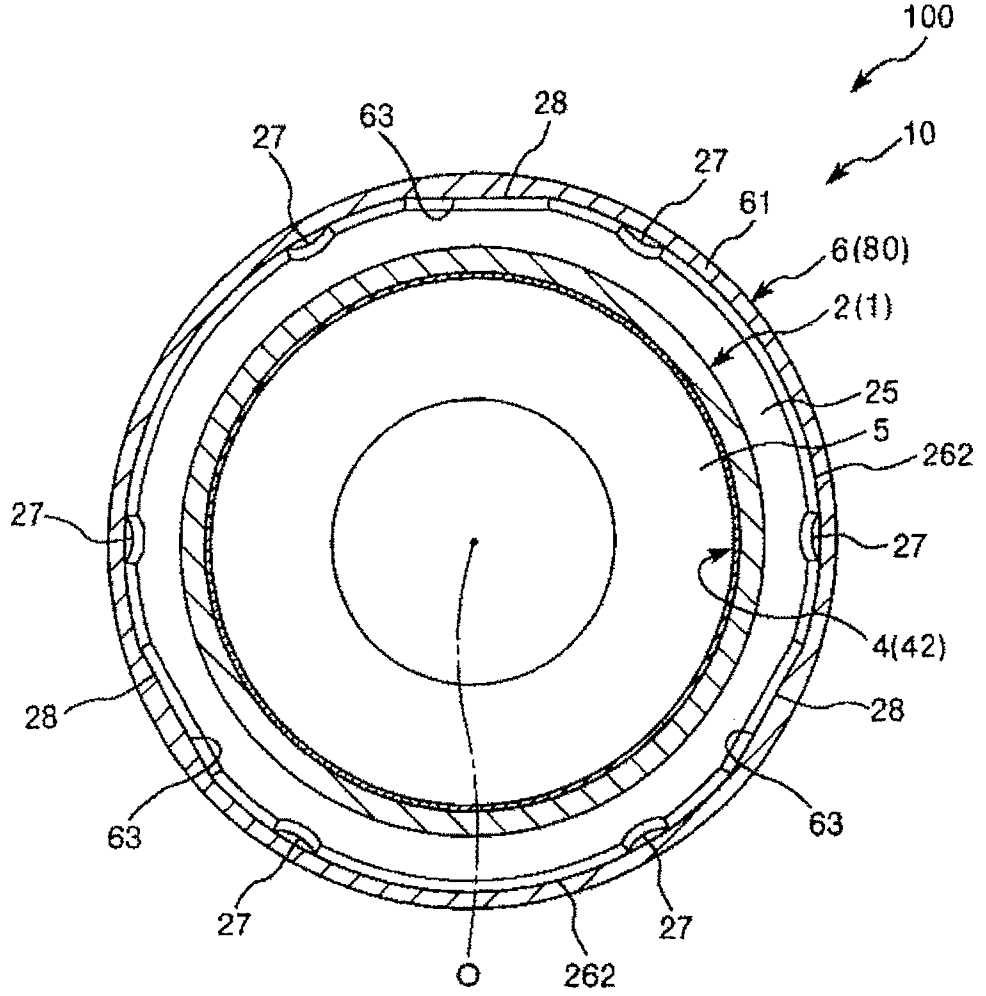
FIG. 6 is a cross-sectional view taken along a line B-B in FIG. 5.
Figure 11:
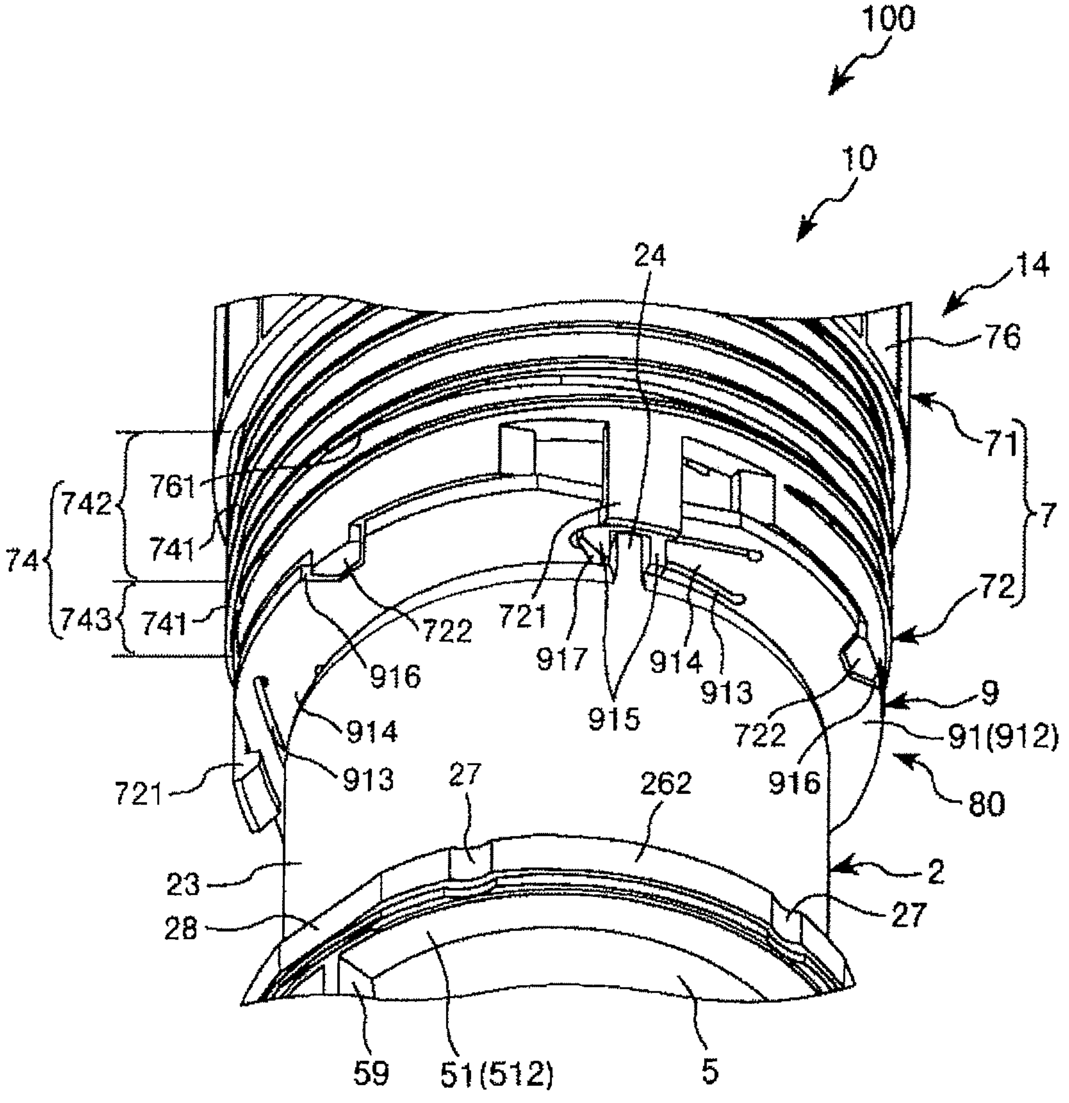
FIG. 11 is a view seen from the direction of an arrow C illustrated in FIG. 7.
Figure 12:
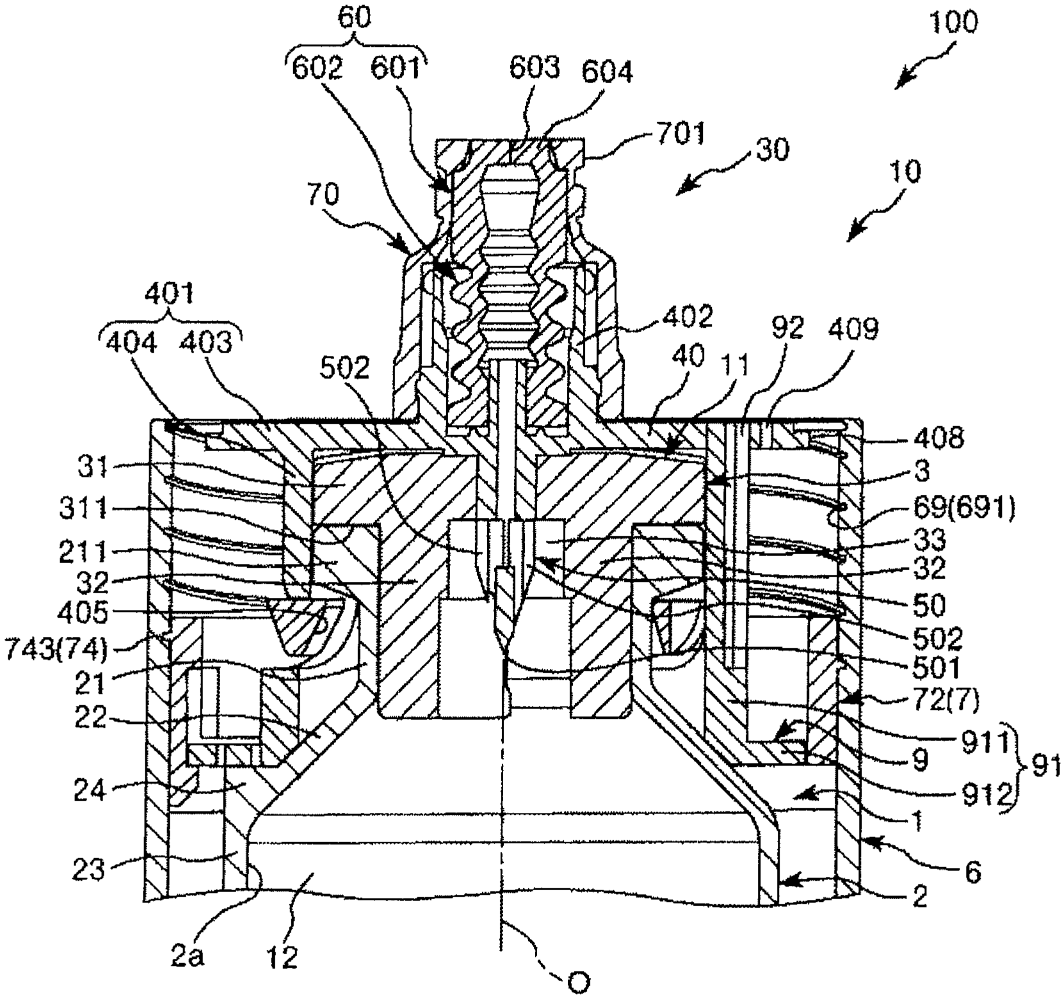
FIG. 12 is a view seen from the direction of an arrow D illustrated in FIG. 9.

FIG. 1 is perspective view illustrating a medical instrument according to an embodiment of the present invention; FIG. 2 is a longitudinal sectional perspective view illustrating the medical instrument illustrated in FIG. 1; FIG. 3 is a view seen from the direction of an arrow A illustrated in FIG. 1; FIG. 4 is a perspective view illustrating an adapter included in the medical instrument according to an embodiment of the present invention; FIG. 5 is a longitudinal sectional perspective view illustrating a state in which the medical container is housed in the medical instrument according to an embodiment of the present invention; FIG. 6 is a cross-sectional view taken along a line B-B in FIG. 5; FIGS. 7 to 10 are longitudinal sectional perspective views illustrating respective operation processes of the medical instrument, in order, according to an embodiment of the present invention; FIG. 11 is a view seen from the direction of an arrow C illustrated in FIG. 7; and FIG. 12 is a view seen from the direction of an arrow D illustrated in FIG. 9. Note that, in the following, the lower side in FIGS. 1 to 5 and FIGS. 6 to 12 will be referred to as “proximal end” or “below (downward)” and the upper side therein will be referred to as “distal end” or “above (upward)” for convenience of description.

As illustrated in the respective drawings, a medical device set 100 includes a medical container 1, a medical instrument 10 (hereafter referred to as “storage instrument”) that houses the medical container 1. Further, the medical device set 100 includes a syringe 20 besides the medical container 1 and the storage instrument 10 (see FIG. 9). Now, configuration of each of the components will be described below.

As illustrated in FIGS. 5 and 7 to 9, the medical container 1 includes a container body 2, a plug body 3 (sealing member), a bag body 4 (balloon), and a protection cover 5. Further, a powdery or liquid medicine P (powdery medicine in the present embodiment) is preliminarily contained inside the medical container 1. This medicine P is mixed with a liquid Q such as a dissolving liquid, a diluting liquid and a medicinal solution supplied from a syringe 20. This mixture is to be a medicinal solution R.

Though not specifically limited, examples of the medicine P include: medicines which are dangerous if erroneously touched by a medical worker, such as carcinostatic agents, immunosuppressant; medicines which has be dissolved in use, such as antibiotic, styptic; medicines required to be diluted, such as pediatric drugs; medicines that requires multi-time dispensing, such as vaccine, heparin, pediatric drugs; medicines such as protein preparation which are easily foamed when dissolved or when sucked into the syringe; and medicines such as anti-body drug in which a small quantity of medicine is contained. In addition, though not specifically limited, an example of the liquid Q may be physiological saline.

The container body 2 is a member formed of a cylindrical body with each of both ends opened. The container body 2 can be divided into a mouth section 21, a shoulder section 22, and a barrel section 23, sequentially from the distal-end side, in accordance with the inside diameter sizes.

Figure 9:
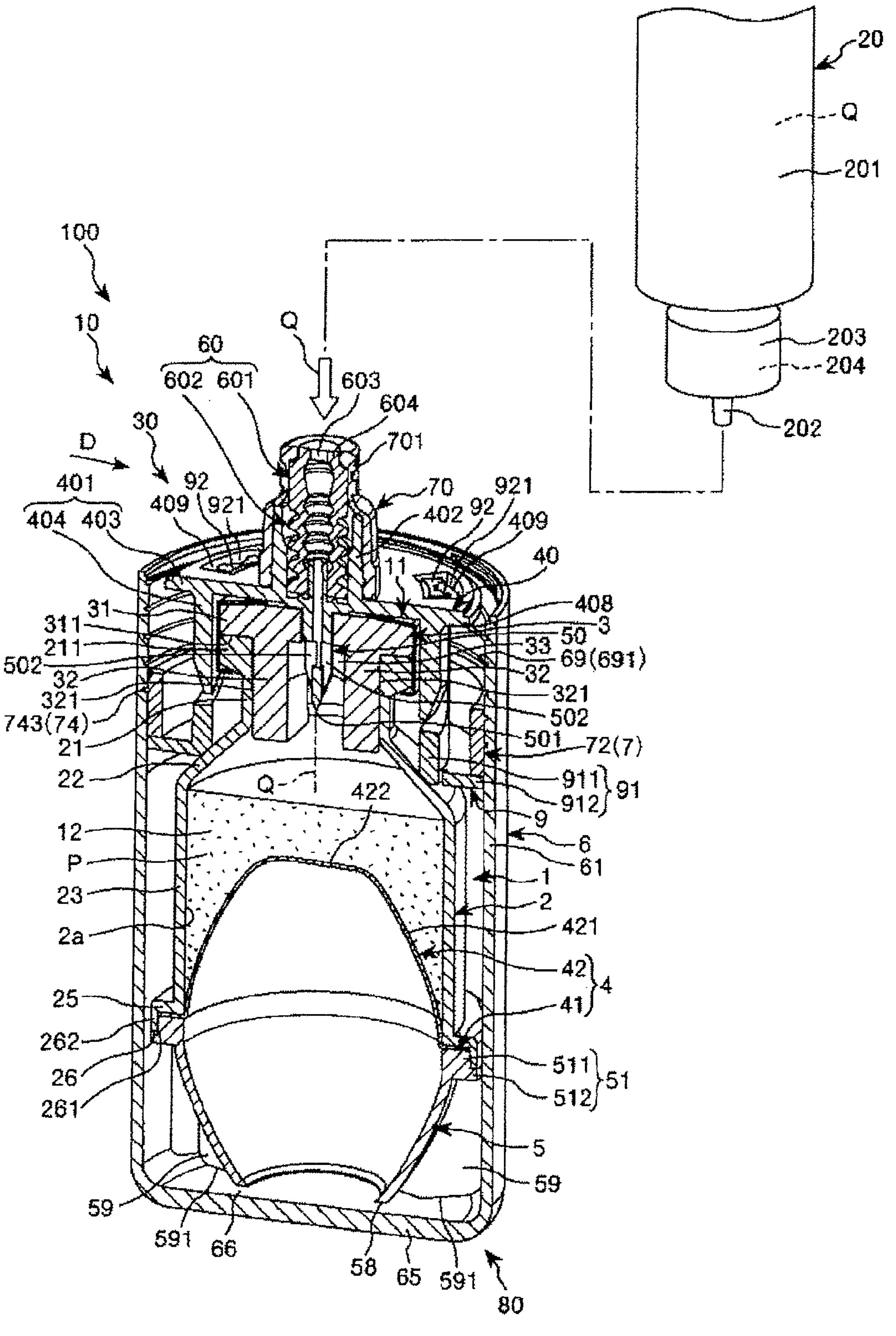
FIG. 9 is a longitudinal sectional perspective view illustrating operation of the medical instrument according to an embodiment the present invention.

The inside diameter of the mouth section 21 is constant along an axial direction, and is smaller than the inside diameter of the barrel section 23. As illustrated in FIG. 9, an adapter 30 (inner structural body) is mounted on the mouth section 21 as a connector included in the storage instrument 10, and the syringe 20 is connected via this adapter 30. Further, the syringe 20 is operated while being connected, thereby allowing the liquid Q to flow from the syringe 20 (see FIG. 9) and the medicinal solution R to flow to the syringe 20 via the mouth section 21.

Further, a ring-shaped projected section 211 is formed on an outer peripheral portion of the mouth section 21 in a projecting manner along a circumferential direction.

The shoulder section 22 is a portion having the inside diameter gradually increasing in a proximal-end direction.

The inside diameter of the barrel section 23 is constant along the axial direction, and is larger than the inside diameter of the mouth section 21. As illustrated in FIG. 11, a plurality of rotation preventing projections 24 (projected portions) is formed upward in a projecting manner in a boundary portion (outer peripheral portion of the container body 2) between the barrel section 23 and the shoulder section 22. The rotation preventing projection 24 can be engaged with a proximal-end side structure body 80 included in the storage instrument 10.

On the proximal-end side of the barrel section 23, a proximal-end opening 261 and a proximal-end edge portion 25 surrounding the proximal-end opening 261 are formed. The proximal-end edge portion 25 is a ring-shaped flange formed along the circumferential direction of the barrel section 23. Further, a proximal-end outer peripheral portion 262 is formed on the outer periphery of the proximal-end edge portion 25 in a manner projecting in the proximal-end direction orthogonal to the proximal-end edge portion 25, and covers the entire outer periphery of the proximal-end edge portion.

The material constituting the container body 2, and other component such as the protection cover 5, is not specifically limited. Examples of the material may include resin material, such as polyolefin like polyethylene, polypropylene, cyclic polyethylene; polyesters such as polyethylene terephthalate; vinyl resins such as polyvinyl chloride resin, polyvinyl alcohol; polyamide such as nylon 6, nylon 6.6, nylon 6.10, nylon 6.12; and other thermoplastic resins. One of these examples or a combination of two or more of these examples may be used. Also, a light shielding additive may be added to cut a specific wavelength. Further, the inner surface of the container body 2 may be coated with, for example, Teflon® or fluorine, to avoid adsorption of the medicine P. The respective components preferably have transparency in order to secure visibility of the inside thereof.

A soft plug body 3 formed of an elastic material is mounted on the mouth section 21 of the container body 2. This ensures the mouth section 21 is sealed in a liquid-tight manner.

As shown in FIGS. 5, 7 to 9, and 12, the plug body 3 includes a top plate 31 formed of a disk-shaped plate, a pair of leg portions 32 projected from a proximal-end surface 311 of the top plate 31, and a tubular section 33 provided between the top plate 31 and the pair of leg portions 32.

The pair of leg portions 32 is formed of plate pieces disposed separately and facing each other. Further, outer surfaces 321 of the leg portions 32 each are formed in an arc-shape along an inner peripheral portion of the mouth section 21. When the pair of leg portions 32 is inserted into the mouth section 21 of the container body 2, the plug body 3 is reliably prevented from being detached from the mouth section 21.

Further, when the pair of leg portions 32 is more deeply inserted into the mouth section 21 of the container body 2, the tubular section 33 tightly contacts the inner peripheral surface of the mouth section 21. Thus, the mouth section 21 is liquid-tightly sealed.

Additionally, the mouth section 21 of the container body 2 is covered with a body cap 11 together with the plug body 3, and the body cap 11 is formed of, for example, aluminum. The body cap 11 is engaged with the projected section 211 of the mouth section 21. This ensures to prevent the plug body 3 from being detached from the mouth section 21 more reliably.

Examples of the elastic material constituting the plug body 3 may include various rubber materials such as natural rubber, isoprene rubber, butadiene rubber, styrene-butadiene rubber, urethane rubber, and fluorine-contained rubber, and various thermoplastic elastomers based on styrene, polyolefin or the like. One of these examples or a combination of two or more of these examples may be used.

As shown in FIGS. 5, 7 to 10, the bag body 4 according to the present embodiment is a member having a bag-like shape, more specifically, having a cup-like shape (bowl-like shape) in a nature state where no external force is applied. Further, a space 12 for containing a medicine is defined by the bag body 4, container body 2, and the plug body 3 in the medical container 1. In this space 12, the medicine P is preliminarily contained.

The bag body 4 includes an edge portion 41 and a reversing part 42 surrounded by the edge portion 41.

As shown in FIG. 5, the edge portion 41 is tightly fixed to the proximal-end edge portion 25 formed on the proximal end of the container body 2. This edge portion 41 is supported by the proximal-end edge portion 25 such that the reversing part 42 folds an edge of the opening section of the bag-shaped bag body 4 outwardly. With this configuration, force is applied to the bag-shaped reversing part 42 in a direction (orthogonal to the axis of the container body 2) in which the reversing part 42 is reversed inside and outside (hereinafter referred to as “inside/outside”) of the bag (the reversing part 42), more specifically, in a direction in which the bag is reversed to a front-side and a back-side of the bag. As a result, the reversing part 42 can be stably and easily reversed.

In the case where the protection cover 5 is not mounted on the container body 2, the edge portion 41 which is a portion to be welded to the container body 2 of the bag body 4 can be protected by the proximal-end outer peripheral portion

262 of the container body 2. For example, even when the container body 2 mounted with no protection cover is directly placed on a table (stand), the container body 2 contacts the table via the proximal-end outer peripheral portion 262. Therefore, the welding portion (edge portion 41) of the bag body 4 can be protected. Also, even when the container body 2 placed on the table moves to a different position on the table, the welding part of the bag body 4 can be protected and the welding portion can be prevented from being damaged in the same manner.

The above-described bag body 4 can be obtained by heating and deforming a flexible sheet material by using, for example, a mold. Suitable molding methods may include vacuum molding and pressure molding. Vacuum molding by a plug assist process is preferable. Further, the thickness t of this sheet material (bag body 4) is not specifically limited. For example, the thickness of the reversing part 42 is preferably from 0.03 to 0.5 mm, and more preferably, from 0.05 to 0.3 mm. Further, the thickness of the edge portion 41 of the bag body 4 is preferably from 0.05 to 0.7 mm, for example, and more preferably, from 0.07 to 0.4 mm. Additionally, the material constituting the sheet material is not specifically limited, and examples may include: polyolefin resin such as polyethylene, polypropylene, cyclic polyethylene; blend resin or copolymerized resin including polyolefin resin; polyester resin such as polyethylene terephthalate; polyamide resin such as nylon; single-layer film such as polyvinylidene chloride, vinyl chloride-polyvinylidene chloride copolymer; single-layer film obtained by vapor-depositing aluminum, silica, and the like on the mentioned single-layer film; multilayer film obtained by laminating the mentioned single-layer films, other film, and metal foil such as aluminum. A material having water-vapor barrier properties or oxygen barrier properties is preferable. A bag body 4 configured to be reversed (reversed inside/outside) can be reliably molded by using the above-mentioned sheet material.

The method of fixing the proximal-end edge portion 25 of the container body 2 to the edge portion 41 is not specifically limited. Examples of the method may include: welding (such as thermal welding, high frequency welding, ultrasonic welding, and laser welding), and bonding (bonding with an adhesive or solvent). Among these methods, the welding method is more preferable.

The reversing part 42 is a portion which is reversed by the liquid Q flowing into the space 12 via the mouth section 21 of the container body 2 (see FIG. 10) and by the medicinal solution R flowing out from the space 12. With the reverse of the reversing part, a rapid inner pressure change inside the space 12 can be suppressed when the syringe 20 performs discharging and sucking. As a result, discharging and sucking can be smoothly performed.

Figure 10:
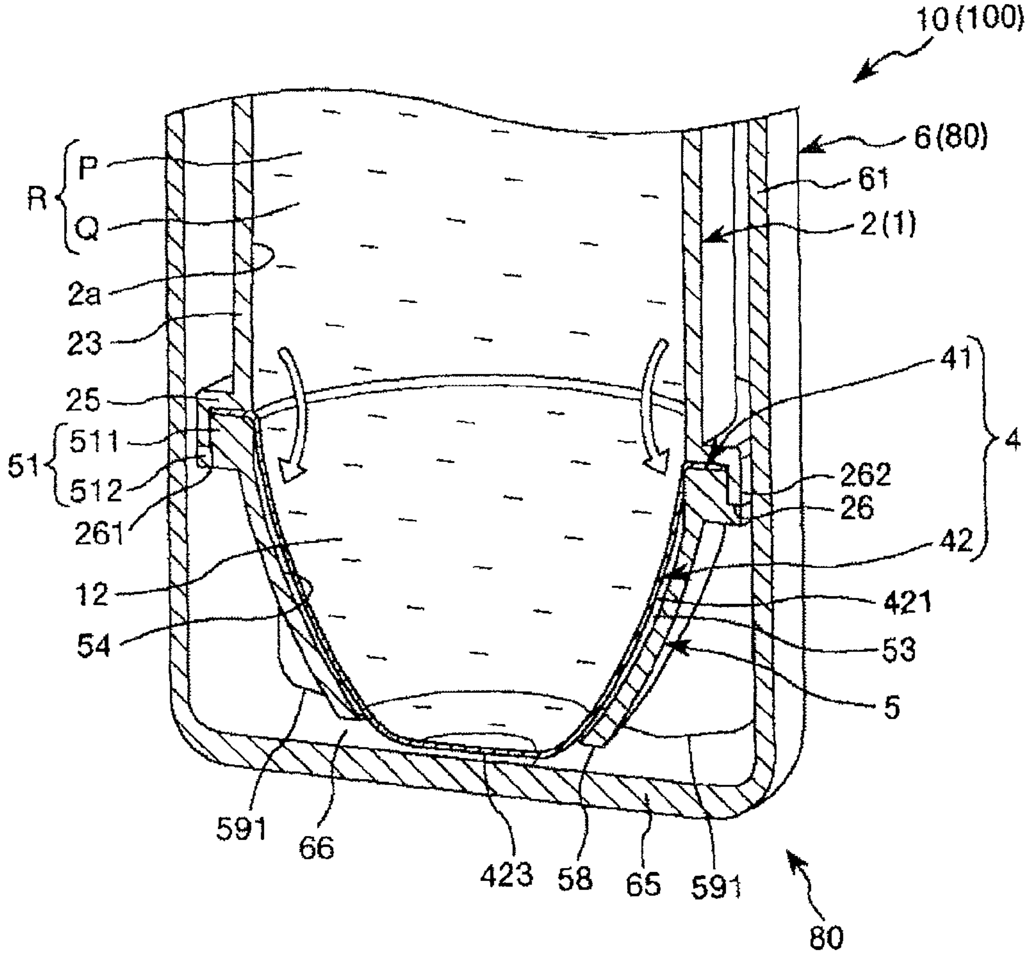
FIG. 10 is a longitudinal sectional perspective view illustrating operation of the medical instrument according to an embodiment of the present invention.

Additionally, the reversing part 42 may take two states: a first state in which the reversing part 42 is expanded toward the distal-end side (see FIGS. 5 and 7 to 9); and a second state in which the reversing part 42 is expanded toward the proximal-end side (see FIG. 10). In the unused state where the medicine P is preliminarily stored in the space 12, the reversing part 42 is in the first state.

Further, the reversing part 42 is positioned inside the barrel section 23 of the container body 2 in the first state, and is protruded from the proximal-end opening 261 of the container body 2 in the second state.

Additionally, in both the first state and the second state, a space-side surface 421 on the space 12 side of the reversing part 42 is separated from an inner peripheral portion 2*a* of the container body 2. In this instance, a separation distance d gradually increases along the axial direction of the container body 2 in a direction away from the edge portion 41. In other words, the distance d gradually increases in a distal-end direction in the first state, and in a proximal-end direction in the second state.

It is preferable that 90% of an entire surface area of the space-side surface 421 of the reversing part 42 be separated from the inner peripheral portion 2*a* of the container body 2, and it is more preferable that 95 to 100% of the entire surface area of the space-side surface 421 of the reversing part 42 be separated from the inner peripheral portion 2*a* of the container body 2.

With the above-described configuration of the reversing part 42, when the medicinal solution R inside the space 12 is sucked to be collected to the syringe 20, the reversing part 42 takes the first state, and the space between the space-side surface 421 of the reversing part 42 and the inner peripheral portion 2*a* of the container body 2 is enlarged toward the mouth section 21 of the container body 2. This allows the medicinal solution R to reliably and easily flow down to the mouth section 21 through the above-described space. As a result, a prescribed amount of the medicinal solution R can be sufficiently, reliably and easily collected.

In the case where the space-side surface 421 of the reversing part 42 contacts (in close contact with) the inner peripheral portion 2*a* of the container body 2 at the time of collecting the medicinal solution R, some of the medicinal solution R may enter between the space-side surface 421 of the reversing part 42 and the inner peripheral portion 2*a* of the container body 2 due to the capillary phenomenon, and may not be sucked and remain therebetween. In such a case, the prescribed amount of the medicinal solution R cannot be collected. In other words, the amount of the collected medicinal solution R is short by the remaining amount.

Therefore, separation of the reversing part 42 from the container body 2 improves a collection rate of the medicinal solution R.

For example, assume that 10 cc of the liquid Q is filled into the space 12 from the syringe 20. This filled amount is a target amount of the medicinal solution to be collected by the collecting operation. When the liquid Q is filled, the reversing part 42 is reversed from the first state to the second state and expands by the filling amount of the liquid Q (10 cc). Then, after the liquid Q is mixed with the medicine P by shaking, collecting operation is executed. The reversing part 42 is reversed from the second state to the first state by the collecting operation and can be returned to the original state by the filling an amount, more specifically, by the amount to be collected (target amount) of medicinal solution. In this instance, the reversing part 42 is separated from the container body 2. In this manner, the target amount of the medicinal solution R can be easily and stably collected.

Additionally, in the unused state illustrated in FIG. 1, the medicine P contacts the entire part of the space-side surface 421 in the first state, and a clearance is generated between the reversing part 42 and the medicine P when the reversing part 42 is reversed from the first state. With this configuration, the liquid Q enters the clearance between the reversing part 42 and the medicine P when the liquid Q is filled into the space 12 from the syringe 20. Therefore, a widest contact area can be secured between the liquid Q and the medicine P. As a result, mixing of the liquid Q with the medicine P is sufficiently and reliably performed and an effect of shortening a time required for dissolving the medicine P with the liquid Q can be obtained.

Even in the case where the medicine P is filled merely up to the level indicated by a two-dot dashed line (virtual line L) in FIG. 5 (in the case where the medicine P does not contact the entire surface of the reversing part 42, namely, the entire part of the space-side surface 421), the clearance is generated between the reversing part 42 and the medicine P when the reversing part 42 is reversed. Therefore, the contact area of the liquid Q and the medicine P is enlarged. In other words, the same effect can be obtained as far as the medicine P at least partly contacts a proximal-end side of the space-side surface 421 in the first state.

In both the first state and the second state, a center part of the reversing part 42 located on an opposite side of the edge portion 41 is formed flat. More specifically, the center part of the reversing part becomes a top portion 422 in the first state and becomes a bottom portion 423 in the second state. Since the center part of the reversing part is formed flat, a volume of the space 12 in the unused state (first state) can be increased without enlarging the container body 2. Additionally, by forming the flat top portion 422 thicker and more constant than a surrounding area thereof, the reversing part 42 can be homogeneously reversed when the reversing part 42 is reversed from the first state to the second state, because reversing starts from the surrounding area of the top portion 422.

As shown in FIGS. 5, and 7 to 10, the protection cover 5 is mounted on the proximal-end section of the container body 2. The protection cover 5 is formed of a cylindrical body having each of both ends opened, and covers the cup-shaped reversing part 42 of the bag body 4 from the proximal-end side thereof. With this configuration, when the reversing part 42 is changed to the second state, expansion of the reversing part 42 can be restricted even though the reversing part 42 tries to expand any further. As a result, a burst in the event of the excessive expansion of the reversing part 42 can be reliably prevented (see FIG. 10). Thus, the protection cover 5 is configured to protect the reversing part 42.

As shown in FIG. 10, when the reversing part 42 is changed to the second state, the reversing part 42 is normally separated from an inner surface 54 of the protection cover 5. In other words, a gap 53 is formed therebetween. With this configuration, the reversing part 42 can be prevented from contacting the inner peripheral portion (inner surface 54) of the protection cover 5 as much as possible. The size of gap 53 is not specifically limited, but is preferably from 0.5 to 2.0 mm, and more preferably from 0.5 to 1.5 mm.

A ring-shaped flange 51 is formed on the distal-end outer peripheral portion of the protection cover 5 in a projecting manner along the circumferential direction. The flange 51 includes a small diameter section 511 and a large diameter section 512 each having different outside diameter, and the small diameter section 511 is positioned more on the distal-end side than the large diameter section 512.

Further, the small diameter section 511 functions as a holding member holding the edge portion 41 of the bag body 4 between the small diameter section and the proximal-end edge portion 25 of the container body 2. By thus holding the edge portion, fixture of the edge portion 41 to the proximal-end edge portion 25 of the container body 2 can be reinforced.

On the other hand, the large diameter section 512 contacts the proximal-end surface 26 of the proximal-end outer peripheral portion 262 of the container body 2. Note that the large diameter section 512 and the proximal-end surface 26 may be fixed by bonding or welding.

Further, a proximal-end surface 58 of the protection cover 5 is separated from a bottom portion 65 of the outer cover member 6 included in the proximal-end side structure body 80. Air can enter and exit the protection cover 5 via a gap 66 between the proximal-end surface 58 of the protection cover 5 and the bottom portion 65 of the outer cover member 6. With this configuration, when a reversing part 42 of the bag body 4 is changed to the second state from the first state, the air is pushed out, and vice versa, the air is sucked. As a result, the reversing part 42 can be easily and reliably reversed.

The air pushed out is released to the atmosphere through a plurality of grooves 27 formed on the outer peripheral surface of the proximal-end outer peripheral portion 262 of the container body 2 (see FIG. 6). According to the configuration shown in FIG. 6, six the grooves 27 are formed, and these grooves 27 are arranged at sense of equal angle around the axis of the container body 2.

As illustrated in FIG. 5, a plurality of blade parts 59 is formed on a part closer to the proximal-end side than the flange 51 of the protection cover 5 on the outer peripheral portion thereof. These blade parts 59 are arranged at equal intervals along the circumferential direction of the protection cover 5. Further, a proximal end 591 of each of the blade parts 59 is projected more on the proximal-end side than the proximal-end surface 58 to contact the bottom portion 65 of the outer cover member 6. With this configuration, the size of the gap 66 (gap length) is restricted, and the gap 66 can be reliably secured.

Next, the syringe 20 will be described.

As illustrated in FIG. 9, the syringe 20 is preliminarily filled with the liquid Q to be mixed with the medicine P. This syringe 20 includes an outer tube 201. The outer tube 201 has a bottomed tubular shape, and the mouth section 202 projected in the distal-end direction is formed on a bottom portion thereof.

Also, the syringe 20 includes a gasket (not shown) liquid-tightly slidable inside the outer tube 201, and a plunger (not shown) connected to the gasket and configured to move and control the gasket inside the outer tube 201. Further, the liquid Q can be discharged from the mouth section 202 with the gasket by pushing the plunger.

Additionally, a ring-shaped lock member (lock adapter) 203 is disposed concentrically with the mouth section 202 on the outer peripheral side of the mouth section 202. A female screw 204 to be screw-engaged with the adapter 30 is formed on an inner peripheral portion of the lock member 203. The syringe 20 is connected to the adapter 30 by this screw-engagement. The lock member 203 may be integrally formed with the mouth section 202, or may be formed separately from the mouth section 202. In the case where the lock member 203 is formed separately from the mouth section 202, the lock member 203 may be supported movable along the axial direction of the mouth section 202, or may be supported rotatable around the axis of the mouth section 202.

The above-described syringe 20 is connected to the medical container 1 via the adapter 30.

Next, a storage instrument 10 will be described.

As illustrated in FIGS. 1 to 12, the storage instrument 10 includes a cap assembly 14 (distal-end side structure body), the adapter 30 disposed inside the cap assembly 14, and the proximal-end side structure body 80.

The cap assembly 14 includes a cap 7 (outer tube body) formed of a cylindrical body and an inner tube body 15 disposed inside the cap 7 and formed of a cylindrical body.

Figure 8:
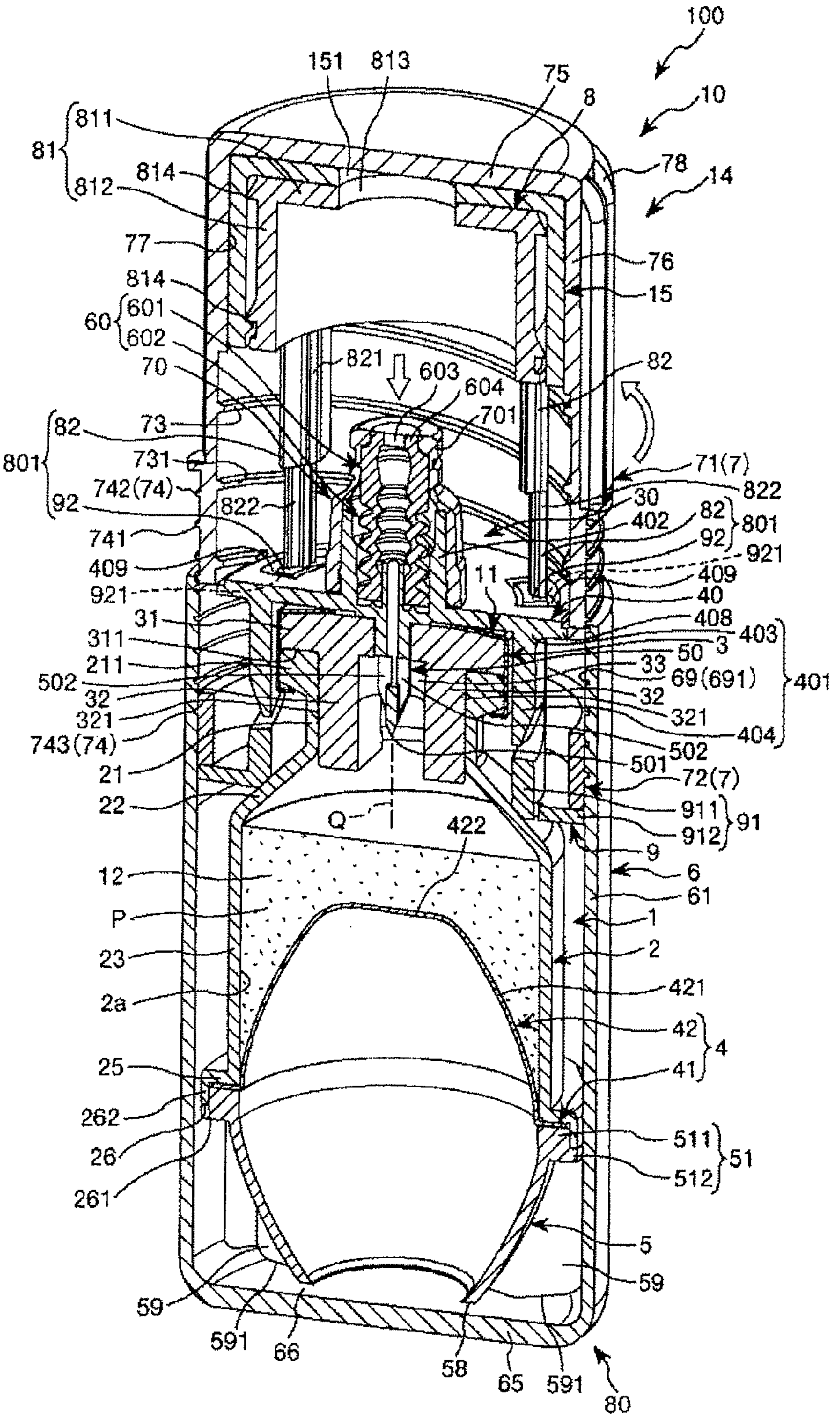
FIG. 8 is a longitudinal sectional perspective view illustrating operation of the medical instrument according to an embodiment of the present invention.

As illustrated in FIGS. 1 and 2, the cap 7 is formed of a top plate 75 and a wall section 76 formed tubular along an edge portion of the top plate 75 and projected from the edge portion in the proximal-end direction. A breaking portion 761 which is breakable is formed halfway in the direction of the center axis O on the wall section 76 of the cap 7, and a cap body 71 positioned on the distal-end side can be separated from a ring portion 72 formed in a ring shape and positioned on the proximal-end side of the cap body 71, interposing the breaking portion 761. Further, as illustrated in FIG. 8, when breaking portion 761 breaks, the cap 7 is separated into the cap body 71 and the ring portion 72. This breakage occurs, as described later, due to rotating force generated by rotating the cap 7 around the center axis O at the time of detaching the cap 7.

The cap body 71 and the ring portion 72 may be formed by mutually connecting different members by welding or bonding, but preferably, both are formed of different kinds of material and two-color molded. This may provide the cap 7 where the breaking portion 761 is surely formed on a boundary portion between the cap body 71 and the ring portion 72. Note that the breaking portion 761 is not limited to the above configuration, and may be formed of a plurality of thin portions intermittently arranged around the center axis O, for example.

Figure 7:
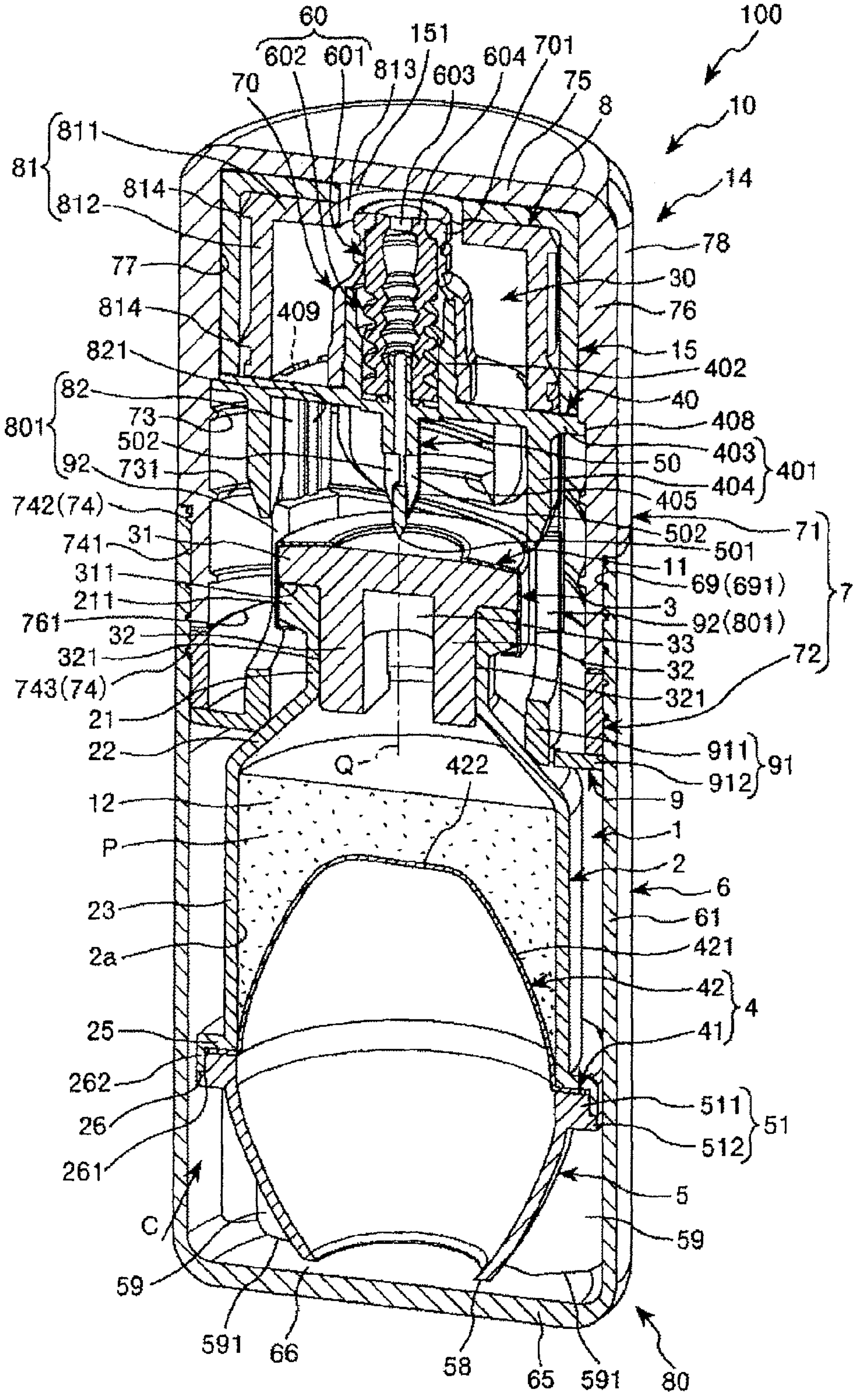
FIG. 7 is a longitudinal sectional perspective view illustrating operation of the medical instrument according to an embodiment of the present invention.

As illustrated in FIGS. 2, 7 and 8, on the wall section 76 (cylindrical body) of the cap 7, a cap-side female screw portion 73 (first cap-side screw-engaged portion) is formed on a part of the proximal-end side of the inner peripheral portion (inner peripheral side), and a cap-side male screw portion 74 (second cap-side screw-engaged portion) is formed on a part of the proximal-end side of the outer peripheral portion (outer peripheral side).

The cap-side female screw portion 73 includes a first screw thread (first screw portion) 731 formed in a spiral shape around the center axis O. This cap-side female screw portion 73 (first screw thread 731) is formed on the cap body 71, but is omitted to be formed on the ring portion 72. More specifically, the cap-side female screw does not reach the ring portion 72.

Also, the cap-side male screw portion 74 includes a second screw thread (second screw portion) 741 formed in a spiral shape around the center axis O. The cap-side male screw portion 74 (second screw thread 741) is formed across the cap body 71 and the ring portion 72, and can be divided into a first male screw portion 742 positioned at the cap body 71 side and a second male screw portion 743 positioned at the ring portion 72 side.

Further, as illustrated in FIG. 2, a pitch $s_1$ between the adjacent first screw threads 731 along the center axis O direction at the cap-side female screw portion 73 is larger than a pitch $s_2$ between the second screw threads 741 along the center axis O at the cap-side male screw portion 74. Also, a formed length $u_1$ of the cap-side female screw portion 73 along the center axis O direction is longer than a formed length $u_2$ of the cap-side male screw portion 74 along the center axis O direction.

Further, the number of turns of the first screw thread 731 in the cap-side female screw portion 73 is equal to or less than the number of turns of the second screw thread 741 in the cap-side male screw portion 74.

In addition, as illustrated in FIG. 1, a plurality of ribs 78 is protrudingly formed, extended in the center axis O direction on the more distal-end side than the cap-side male screw portion 74 located on the outer peripheral portion on the cap 7. These ribs 78 are arranged at intervals of equal angle around the center axis O. The ribs 78 thus configured can prevent fingers from slipping off the cap 7 when the cap 7 is gripped with the fingers and rotated around the center axis O. Accordingly, the rotating operation can be stably executed.

A diameter-reduced section 77 having a reduced inside diameter is formed on the more distal-end side than the cap-side female screw portion 73 located on the inner peripheral portion of the cap 7 (cap body 71).

The inner tube body 15 is disposed concentrically with the diameter-reduced section 77 and fixed to the diameter-reduced section 77. This fixing method is not specifically limited, and for example, welding (thermal welding, high frequency welding, ultrasonic welding, and the like) and bonding (bonding with an adhesive or solvent) may be used.

The material constituting the cap 7 and the inner tube body 15 is not specifically limited, and for example, the material same as the container body 2 of the medical container 1 may be used.

Inside the cap 7, the adapter 30 is disposed movable in the proximal-end direction. As illustrated in FIGS. 2, 4, 7 to 9 and 12, the adapter 30 includes a main body 40, a bottle needle 50 (hollow needle), a valve body 60, and a cap 70 (adapter-side cap).

The main body 40 includes a mounting section 401 (adapter-side mounting section) to be mounted on the mouth section 21 of the container body 2, a valve body installation section 402 where valve body 60 is installed, and an adapter-side male screw portion 408 (adapter-side screw-engaged portion) to be screw-engaged with the cap-side female screw portion 73 of the cap 7.

The mounting section 401 is substantially tubular in overall shape, and more specifically, includes a top plate 403 and a plurality of projecting pieces 404 projected from a lower surface of the top plate 403, and can be fitted with the mouth section 21 of the container body 2 from outside thereof. A pawl 405 is formed in a projecting manner inside each of the projecting pieces 404. As illustrated in FIG. 12, each pawl 405 is engaged with the projected section 211 of the mouth section 21 when the mounting section 401 is fitted with the mouth section 21 of the container body 2. With this configuration, the adapter 30 can be reliably prevented from unexpectedly being detached from the container body 2.

Also, the adjacent projecting pieces 404 are separated each other. This allows the respective projecting pieces 404 of the mounting section 401 to expand in a radial direction when the pawls 405 climb over the projected section 211 of the mouth section 21 in the process of fitting the mounting section 401 to the mouth section 21. With this configuration, the mounting section 401 is easily mounted on the mouth section 21.

As illustrated in FIG. 4, a plurality of guide holes 409 (three guide holes in the drawing) is formed penetrating the top plate 403 in a thickness direction thereof. A guide portion 801 included in the proximal-end side structure body 80 is inserted into each of the guide holes 409. When the adapter 30 moves in the proximal-end direction, the adapter 30 can be guided by the guide portion 801. More specifically, an arm portion 82 of a first guide member 8 (distal-end side guide member) is inserted into each guide hole 409, and when the adapter 30 moves in the proximal-end direction, the adapter 30 can be guided by the guide portion 801 including the arm portion 82 of the first guide member 8 and an arm portion 92 of a second guide member 9 (proximal-end side guide member).

The valve body installation section 402 is formed on a center part of the top plate 403 in a manner projecting in the distal-end direction and has a tubular shape. The valve body 60 can be inserted into the valve body installation section.

As illustrated in FIG. 4, the adapter-side male screw portion 408 includes a projected section 406 formed in a ring shape on the outer peripheral portion (edge portion) of the top plate 403 along the circumferential direction thereof, and is a portion where a plurality of grooves 407 is formed halfway in a direction forming the projected section 406. Each groove 407 is formed in an inclined manner with respect to the center axis O. Further, the first screw thread 731 of the cap-side female screw portion 73 of the cap 7 can be engaged with, more specifically, inserted into each groove 407. Thus, the adapter-side male screw portion 408 is screw-engaged with the cap-side female screw portion 73.

As illustrated in FIG. 2, a bottle needle 50 is disposed on the proximal-end surface of the top plate 403 of the mounting section 401 concentrically with the valve body installation section 402. This bottle needle 50 includes a sharp needle tip 501 that can puncture the top plate 31 of the plug body 3 of the medical container 1. Also, the bottle needle 50 is a hollow needle and includes at least one side hole 502 (two side holes in the present embodiment) opened at the side surface thereof.

The valve body 60 is formed of a tubular elastic body that communicates with the bottle needle 50, and can be divided into a head section 601 on the distal-end side and a barrel section 602 on the proximal-end side. The head section 601 includes a top plate 604 on which a slit 603 having self-closing property is formed. When the syringe 20 is connected to the adapter 30, the mouth section 202 of the syringe 20 presses and deforms the top plate 604, thereby opening the slit 603. When the syringe 20 starts discharging or sucking in this state, the liquid can flow between the syringe 20 and the medical container 1 via the valve body 60 and the bottle needle 50. Further, when the syringe 20 is detached from the head section 601, the pressing force against the top plate 604 is released, thereby closing the slit 603.

The barrel section 602 has a bellows shape, and functions as a biasing section for biasing the head section 601 in the distal-end direction. As a result, while the syringe 20 is detached, the head section 601 can stay in a designated position with respect to the cap 70.

The cap 70 is a tubular member covering the valve body 60. The proximal-end inner peripheral portion of this cap 70 is joined to the outer peripheral portion of the valve body installation section 402 of the main body 40. Also, the top plate 604 of the head section 601 of the valve body 60 located at the designated position can be compressed at the distal-end outer peripheral portion of the cap 70. This reliably closes the slit 603.

Further, a male screw 701 is formed on the outer peripheral portion of the cap 70. The female screw 204 of the lock member 203 of the syringe 20 can be screw-engaged with the male screw 701.

Thus, in the adapter 30, the valve body 60 and the cap 70 function as the connectors to be connected to the syringe 20. Therefore, when the syringe 20 is connected with the adapter 30(connector), the syringe 20 and the space 12 of the medical container 1 (container body 2) communicate each other via the deformed valve body 60 and the bottle needle 50 as described above. In this state, the liquid can flow between the syringe 20 and the medical container 1.

The material constituting the main body 40, bottle needle 50, and cap 70 is not specifically limited, and for example, the material same as the container body 2 of the medical container 1 may be used. Also, the material constituting the valve body 60 is not specifically limited, and for example, the material same as the plug body 3 may be used.

As illustrated in FIGS. 1 to 3 and 5 to 12, the proximal-end side structure body 80 includes the outer cover member 6, the first guide member (distal-end side guide member) 8, and the second guide member (proximal-end side guide member) 9.

As illustrated in FIG. 5, the outer cover member 6 is a member having a bottomed tubular shape. The outer cover member 6 can house the medical container 1 inside the housing section 61 thereof. With this configuration, the container body 2 is covered with the outer cover member 6. Therefore, in the case where the medicine P includes any medicine which is dangerous if erroneously touched by a medical worker, it is possible to prevent contamination of the circumference and to secure safety for the medical worker even though the medicine P is stuck to the outer surface of the container body 2 while, for example, manufacturing the medical container 1. Additionally, the medical container 1 can be held via the outer cover member 6 same as the vial container in the related art.

A proximal-end side female screw portion (proximal-end side screw-engaged portion) 69 is provided on the inner peripheral portion of the outer cover member 6. The proximal-end side female screw portion 69 includes a groove (screw groove) 691 formed in a spiral shape around the center axis O. Accordingly, the second screw thread 741 of the cap-side male screw portion 74 of the cap 7 can be engaged with, more specifically, inserted into the groove 691. This allows the proximal-end side female screw portion 69 to be screw-engaged with the cap-side male screw portion 74. A formed length of the proximal-end side female screw portion 69 along the center axis O direction is same as the formed length $u_2$ of the cap-side male screw portion 74.

Also, as illustrated in FIG. 6, a plurality of flat sections 63 (restricting sections) is formed on the inner peripheral portion of the outer cover member 6, but in a position different from where the proximal-end side female screw portion 69 is formed (according to the configuration in FIG. 6, three flat sections are formed at equal intervals in a circumferential direction of the outer cover member 6). The respective flat sections 63 can individually abut on a plurality of flat sections 28 formed on the outer peripheral surface of the proximal-end outer peripheral portion 262 of the container body 2 (according to the configuration illustrated in FIG. 6, three flat sections are formed at equal intervals in the circumferential direction of the container body 2). This prevents the container body 2 from rotating around the center axis O with respect to the outer cover member 6. By thus restricting the rotation, when the syringe 20 is connected to the adapter 30 mounted on the container body 2 by screw-engagement while holding the outer cover member 6, the connecting work can be easily performed. According to the configuration illustrated in FIG. 6, the flat sections 63 and the flat sections 28 are provided as the restricting sections to prevent the container body 2 from rotating around the center axis O with respect to the outer cover member 6. However, the configuration is not limited thereto, and for example, the restricting section may be configured by engaging projected sections with recessed section respectively formed on the outer peripheral surface of the container body 2 and the inner peripheral surface of the outer cover member 6 or may be configured by fitting the outer cover member 6 to the container body 2.

Thus, the outer cover member 6 is configured to include the housing section 61 and the proximal-end side female screw portion 69.

As illustrated in FIG. 2, the first guide member 8 includes a main body 81 and a plurality of arm portions 82 (three arm portions in the present embodiment) formed in a projecting manner from the main body 81 in the proximal-end direction.

The main body 81 includes a top plate 811 and a wall section 812 formed tubular along an edge portion of the top plate 811 and projected from the edge portion in the proximal-end direction. This main body 81 is positioned inside the inner tube body 15 of the cap 7.

In the center part of the top plate 811, a through-hole 813 penetrating the top plate in the thickness direction is formed. Also, a through-hole 151 is formed in the inner tube body 15 at a position where the through-hole 813 faces. While the cap 7 is not yet detached (in the unused state), a distal-end portion of the cap 70 of the adapter 30 is inserted into at least the through-hole 813 out of the through-holes 813 and 151 (see FIG. 2). The entire length of the storage instrument 10 can be shortened by this inserted portion, thereby contributing to size reduction of the storage instrument 10.

A plurality of projected portions 814 (two projected portions in the present embodiment) formed in a ring shape along the circumferential direction is formed on the outer peripheral portion of the wall section 812. Each of the projected portions 814 can be engaged with the inner peripheral portion of the inner tube body 15. This engagement can stably prevent the first guide member 8 from being detached from the inner tube body 15.

Each of the arm portions 82 is extended from the proximal end of the wall section 812. A rib 821 along the longitudinal direction is formed on the inner surface of each of the arm portion 82 in a projecting manner. The rib 821 reinforces the arm portion 82 and surely prevents unexpected deform such as bending.

Additionally, a projection 822 extending further in the proximal-end direction is provided in each of the arm portions 82. The projection 822 is inserted into a recess 921 of the arm portion 92 included in the second guide member 9. This insertion prevents the first guide member 8 and the second guide member 9 from relatively rotating.

As illustrated in FIG. 2, the second guide member 9 includes a main body 91 and a plurality of arm portions 92 (three arm portions in the present embodiment) formed in a projecting manner in the distal-end direction from the main body 91.

The main body 91 is a mounting section (proximal-end side mounting section) to be mounted on the container body 2 of the medical container 1, and includes a ring-like portion 911 formed in a ring shape and a flange 912 formed on the outer peripheral portion of the ring-like portion 911 in a projecting manner.

As illustrated in FIGS. 3 and 11, three slits 913 formed in a U-shape are formed on the flange 912. A portion surrounded by each of the slits 913 is an elastic piece 914 that elastically deforms. Further, the elastic piece 914 includes an engagement portion 915 where the projected portion 24 of the container body 2 of the medical container 1 is sandwiched and engaged. Since the engagement portion 915 is engaged with the projected portion 24, rotation of the second guide member 9 and the first guide member 8 (guide portion 801) together with the cap 7 is prevented at the time of rotating the cap 7 around center axis O in order to detach the cap, thereby surely achieving to restrict the guide members from rotating around the center axis O. With this configuration, the adapter 30 surely moves in the proximal-end direction, more specifically, to the medical container 1 to be surely mounted on the medical container 1.

As a result, the above-described rotating restriction surely prevents the guide portion 801 from rotating with respect to the outer cover member 6.

Components that function as the rotation restricting unit besides the engagement portion 915, such as the projected portion 24, flat sections 28 of the container body 2, and the flat sections (restricting section) 63 of the outer cover member 6, perform the rotation restricting function when all of these components interact together.

Meanwhile, the cap 7 includes a detachment preventing section 721 configured to prevent the second guide member 9 (guide portion 801) from being detached. This detachment preventing section 721 is a means for fixing the ring portion 72 to a guide structure body later described, projected from the ring portion 72, and includes a plurality of pawls to be engaged with a flange 912 of the second guide member 9.

Also, the cap 7 includes a plurality of projections 722 (three projections in the present embodiment) in a position different from detachment preventing section 721 of the ring portion 72. Each projection 722 is inserted into a recess 916 provided at the flange 912 of the second guide member 9. This prevents the second guide member 9 from rotating with respect to the cap 7.

As illustrated in FIG. 2, each of the arm portions 92 is positioned on an extension line of each of the arm portions 82 of the first guide member 8, and the corresponding arm portion 82 is engaged (inserted) in a disengageable manner. In the proximal-end side structure body 80 under such a state, one arm portion 82 and one arm portion 92 constitute one long portion along the center axis O, constituting the guide portion (long portion) 801 that guides the adapter 30. Each guide portion 801 passes through each guide hole 409 of the adapter 30. With this configuration, when the adapter 30 moves in the proximal-end direction at the time of rotating and detaching the cap 7, the adapter 30 is guided along the moving direction and also the adapter 30 can be restricted from rotating together with the cap 7.

Additionally, as described above, each of the guide portions 801 is formed of one arm portion 82 and one arm potion 92, and the projection 822 of the arm portion 82 is inserted into the recess 921 of the arm portion 92 in an assembled state (finished with assembly), but the arm portion 82 (distal-end side portion) and the arm portion 92 (proximal-end side portion) are separated while detaching the cap 7.

The material constituting the outer cover member 6, first guide member 8, and second guide member 9 is not specifically limited. For example, the material same as the container body 2 of the medical container 1 may be used.

Next, a description will be given for an assembling work whereby the unused medical container 1 including the space 12 preliminarily filled with the medicine P is housed and assembled inside the storage instrument 10.

The storage instrument 10 is preliminarily separated into a first assembly 101 illustrated in FIG. 2 (same as FIGS. 1 and 3) and a second assembly 102 illustrated in FIG. 5.

The first assembly 101 is in an assembled state (including the guide structure body where the guide portion 801 and the main body 91 (mounting section) are integrated) obtained by housing and assembling the first guide member 8 and the second guide member 9 in the cap assembly 14 out of the adapter 30, the outer cover member 6 constituting the proximal-end side structure body 80, the first guide member 8, and the second guide member 9. The assembly is carried out as next.

First, each of the arm portions 82 of the first guide member 8 is inserted into each guide holes 409 of the adapter 30. The insertion is executed until the wall section 812 of the main body 81 of the first guide member 8 abuts on the top plate 403 of main body 40 of the adapter 30.

Then, the adapter 30 to which the first guide member 8 is inserted is rotated in a prescribed direction, thereby screw-engaging the adapter-side male screw portion 408 of the adapter 30 with the cap-side female screw portion 73 of the cap 7 of the cap assembly 14. This screw-engagement is executed until the top plate 403 of the adapter 30 abuts on the diameter-reduced section 77 of the cap 7, or until the top plate 811 of the first guide member 8 abuts on the inner tube body 15 of the cap assembly 14. This allows the adapter 30 and the first guide member 8 to be housed inside the cap assembly 14. At this point, note that the first guide member 8 can be engaged with the inner peripheral portion of the inner tube body 15 at each of the projected portions 814 as described above. Therefore, detachment from the inner tube body 15 (cap assembly 14) is prevented.

Next, the second guide member 9 is inserted into the cap assembly 14 where the adapter 30 and the first guide member 8 are housed. At the same time, each of the arm portions 82 of the first guide member 8 is inserted into each of the arm portions 92 of the second guide member 9 up to an insertion limit. In this instance, a flange 912 of the main body 91 of the second guide member 9 is engaged with the detachment preventing section 721 of the cap 7, and also the projection 722 of the cap 7 is inserted into the recess 916 of the second guide member 9 (see FIG. 3). This restricts a mutual positional relation around the center axis O between the cap assembly 14 and the second guide member 9. This also restricts the mutual positional relation around the center axis O between the first guide member 8 and the second guide member 9. Therefore, the mutual positional relation around the center axis O among the cap assembly 14, the first guide member 8, and the second guide member 9 is restricted (see FIG. 2).

The first assembly 101 is obtained by the above-described assembly.

On the other hand, the second assembly 102 is in an assembled state obtained by housing and assembling the medical container 1 in the outer cover member 6. This assembly is executed by inserting the medical container 1 into the outer cover member 6 from the proximal-end side. At this point, as described above, each of the flat sections 63 formed on the inner peripheral portion of the outer cover member 6 mutually abuts on the each of the flat sections 28 formed on the proximal-end outer peripheral portion 262 of the container body 2, thereby restricting the medical container 1 from rotating around the center axis O with respect to the outer cover member 6 (see FIG. 6).

The second assembly 102 is obtained by the above-described assembly.

Further, the first assembly 101 and the second assembly 102 assembled as described above are assembled with one another. This assembly will be executed as follows.

First, the proximal-end side of the first assembly 101 is rotated around the center axis O in a predetermined direction toward the second assembly 102 so as to screw-engage the cap-side male screw portion 74 of the cap 7 of the first assembly 101 with the proximal-end side female screw portion 69 of the second assembly 102. In this instance, as described above, the mutual positional relation among the cap assembly 14, first guide member 8 and second guide member 9 around the center axis O is restricted at the first assembly 101. This allows the adapter 30, first guide member 8, and second guide member 9 to be rotated all together with the cap assembly 14 only on the condition that the rotation around the center axis O is executed holding the cap assembly 14 when the first assembly 101 is mounted on the second assembly 102 by screw-engagement.

Further, when screw-engagement between the first assembly 101 and the second assembly 102 is advanced, an inclined surface 917 of the engagement portion 915 of each of the elastic pieces 914 at the second guide member 9 finally climbs over the rotation preventing projection 24 of the container body 2 of the medical container 1, and is engaged with the rotation preventing projection 24. Here, the screw-engagement stops (see FIG. 11). The inclined surface 917 is formed on a forward part of the rotating direction. The elastic piece 914 can be elastically deformed when the inclined surface 917 climbs over the rotation preventing projection 24. Further, this engagement can surely restrict the rotation of the first guide member 8 and second guide member 9 around the center axis O with respect to the medical container 1 (second assembly 102) as described above.

With this assembly, the storage instrument 10 housing the medical container 1 is obtained.

Next, an operating method (using method) for the storage instrument 10 housing the medical container 1 will be described mainly referring to FIGS. 7 to 10.

[1] First, as illustrated in FIG. 7, the unused storage instrument 10 housing the medical container 1 is prepared. Also, the syringe 20 filled with a just right amount of the liquid Q to be sufficiently mixed with the medicine P inside the medical container 1 is prepared.

[2] Next, as illustrated in FIG. 8, while holding the cap 7 of the cap assembly 14, the cap assembly 14 is rotated around the center axis O in a direction (direction of an arrow in FIG. 8) opposite to the above mentioned direction (direction at the time of assembling work). Due to the operating force (rotating force) at the time of this rotating operation, the cap body 71 is rotated together with the inner tube body 15 with respect to the outer cover member 6; however, rotation of the ring portion 72 with respect to the outer cover member 6 is restricted by the engagement between the projection 722 and the recess 916 of the second guide member 9, engagement between the engagement portion 915 of the second guide member 9 and the projected portion 24 of the container body 2, and engagement between the flat sections 28 of the container body 2 and the flat sections 63 of the outer cover member 6. Accordingly, the breaking portion 761 located between the cap body 71 and the ring portion 72 breaks, exceeding a breaking limit, thereby separating the cap body 71 from the ring portion 72.

Subsequently, as the cap body 71 is continuously rotated, the cap body 71 moves in the distal-end direction while screw-engagement between the first male screw portion 742 (cap-side male screw portion 74) and the proximal-end side female screw portion 69 of the outer cover member 6 (proximal-end side structure body 80) is released. At this point, the first guide member 8 also moves in the distal-end direction together with the cap body 71 because the first guide member 8 is connected to the cap body 71 via the inner tube body 15.

Also, as described above, the pitch $s_1$ at the cap-side female screw portion 73 is set larger than the pitch $s_2$ at the cap-side male screw portion 74. This prevents the adapter 30 screw-engaged with the cap-side female screw portion 73 from rotating at each of the guide portions 801 (arm portion 82, 92) when the cap body 71 is rotated, and at the same time the adapter moves in the proximal-end direction along the guide portion 801 by a distance corresponding (equivalent) to rotation of the cap body 71. Note that a total moved distance of the adapter 30 is equal to: ((one pitch length at cap-side female screw portion 73)−(one pitch length at cap-side male screw portion 74))×(number of turns of cap-side female screw portion 73).

After that, when screw-engagement with the outer cover member 6 is completely released, the cap body 71 is detached from the outer cover member 6. In this instance, the number of turns of the first screw thread 731 at the cap-side female screw portion 73 is equal to or less than the number of turns of the second screw thread 741 at the cap-side male screw portion 74. Accordingly, the adapter 30 moves the above-mentioned total moved distance, and the adapter-side male screw portion 408 is detached from the cap-side female screw portion 73. Simultaneously, the bottle needle 50 penetrates the plug body 3 of the medical container 1, and consequently, the inside of the medical container 1 (space 12) communicates with the outside via the bottle needle 50.

Further, as described above, since each of the guide portions 801 is formed of the arm portions 82 and 92 mutually engaged in a disengageable manner, the arm portion 82 and arm portion 92 can be separated halfway in the longitudinal direction. When the cap body 71 is detached from the outer cover member 6 by this separation, the first guide member 8 including the arm portion 82 is pulled to (remaining on) the cap body 71 side while the second guide member 9 including the arm portion 92 remains on the ring portion 72 side. Thus, the first guide member 8, particularly the arm portion 82, can be detached together with the cap body 71. As a result, connecting the syringe 20 to the adapter 30 in the next step can be easily executed (see FIG. 9).

[3] Next, the syringe 20 is connected to the adapter 30 that communicates with the medical container 1 as illustrated in FIG. 9 (hereinafter, this state is referred to as "connected state"). The above connecting work is carried out by screw-engaging the female screw 204 of the lock member 203 of the syringe 20 with the male screw 701 of the cap 70 of the adapter 30. Further, as described above, since rotation of the adapter 30 with respect to the container body 2 of the medical container 1 is restricted by the arm portion 92 during the connecting work, the connecting work can be stably carried out. Since rotation of the outer cover member 6 with respect to the container body 2 is also prevented, the above connecting work can be carried out while holding the outer cover member 6.

Further, in the connected state, the slit 603 of a valve body 60 of the adapter 30 is in an open state as described above.

[4] Next, in the connected state, the plunger of the syringe 20 is pushed to supply the liquid Q from the syringe 20 to the space 12 of the medical container 1 as shown in FIG. 10. The liquid Q flows down through the valve body 60 and the bottle needle 50, and then flows into the space 12 through the side hole 502 of the bottle needle 50. Thus, the liquid Q is mixed with the medicine P, and the medicinal solution R starts to be produced.

Further, the reversing part 42 of the bag body 4 is changed to the second state, being pressed by the liquid Q which has flown into the space 12. As a result, the volume of the space 12 is increased, whereby an excessive increase of the inner pressure of the space 12 caused by pushing the plunger can be suppressed. Thus, it is possible to omit the pressure which is necessary in the related to control the pressure inside the vial container containing the powdery medicine required to be dissolved by sucking the air into the syringe from the vial container by the amount of the dissolving liquid to be injected.

After that, the medicine P is completely dissolved in the liquid Q by shaking, and the medicinal solution R is produced. In this instance, the liquid Q enters between the reversing part 42 and the medicine P as described above, and a contact area between the liquid Q and the medicine P is enlarged, whereby the liquid Q and the medicine P can be sufficiently and surely mixed. As a result, the shaking time can be shortened.

[5] Subsequently, the medical container 1 is turned upside down together with the outer cover member 6 while keeping the connected state. Then, the plunger of the syringe 20 is pulled to collect the medicinal solution R into the syringe 20. In this instance, the reversing part 42 of the bag body 4 is pulled together with the medicinal solution R, and changed to the first state. At this point, the space-side surface 421 is separated from the inner peripheral portion 2*a* as described above. Therefore, the medicinal solution R can easily and reliably flow down to the mouth section 21 of the container body 2, passing between the space-side surface 421 of the reversing part 42 and the inner peripheral portion 2*a* of the container body 2. As a result, the medicinal solution R can be easily and reliably collected. Also, since the reversing part 42 returns to the first state, it is possible to prevent the pressure inside the container body 2 (space 12) from being negative during the sucking operation. Thus, the pressure control can be omitted although it has been necessary in the related art to control the pressure inside the vial container containing the powdery medicine required to be dissolved by returning the air from the syringe to the vial container by the amount of the medicinal solution sucked into the syringe.

In the case where the medicinal solution R is preliminarily filled inside the container body 2, the reversing part 42 in the unused state is in the second state. Accordingly, when the medicinal solution R is collected to the syringe 20, the reversing part 42 is changed to the first state. Therefore, it is possible to prevent the pressure inside the container body 2 (space 12) from being negative at the time of sucking. Also, it is possible to omit the pressure control in which the air is returned to the vial container from the syringe by the amount of the medicinal solution sucked into the syringe.

Thus, in the storage instrument 10 having the above-described configuration, the adapter 30 is mounted on the medical container 1, interlocking with detachment of the cap 7, i.e., detachment operation. On the other hand, for example, in the storage instrument of the related art, which includes the cover having a bottomed tubular shape and the cap to be detachably mounted on the distal-end opening of the cover and houses the medical container, the cap is detached from the cover and then the adapter is mounted on the medical container after detaching the cap. Further, in the storage instrument 10, such bothersome operation (work) of mounting the adapter again on the medical container after detaching the cap, executed in the storage instrument of the related art, can be omitted. Therefore, according to the present storage instrument 10, the medical container 1 can be used immediately after detaching the cap 7, thereby achieving excellent operability.

While the embodiment of the medical instrument illustrated in the drawings has been described above, the present invention is not limited thereto, and each of the components of the medical instrument can be replaced with a constituent element that can exhibit an equivalent function. Further, arbitrary constituent elements may be added.

Further, according to the present embodiment, the number of the guide portions to guide the adapter at the proximal-end side structure body is three, but is not limited thereto, and the number of the guide portions may be, for example, one, two, or more than three.

Also, the second cap-side screw-engaged portion may be formed more on the proximal-end side than the first cap-side screw-engaged portion on the inner peripheral surface of the cap (cylindrical body).

Further, the first screw portion and second screw portion are formed of the respective screw threads according to the present embodiment, but not limited thereto, and may be formed of screw grooves. For instance, in the case where the second screw portion is formed of the screw groove, the proximal-end side screw-engaged portion to be screw-engaged therewith is formed of the screw thread.

Further, a rotation preventing unit is configured at least to restrict rotation of the guide portion with respect to the outer cover member. For example, when the cap is mounted on the outer cover member, it may be configured that the mounting section is fitted to the outer cover member. In this case, a ring member can be omitted.

Also, the rotation preventing unit may be configured that the ring member and the outer cover member are fitted with projections and recesses, and the like such that rotation of the ring member and the outer cover member can be relatively restricted when the cap is mounted on the outer cover member by screw-engagement.

Further, the rotation preventing unit may be configured without the ring member but providing the screw-engaged portion to be engaged with the proximal-end side screw-engaged portion at the mounting section such that the mounting section and the outer cover member are engaged with projections and recesses, and the like to relatively restrict the rotation of the mounting section and the outer cover member when the cap is mounted on the outer cover member by screw-engagement.

Moreover, by thus configuring the rotation preventing unit, the projected portion of the container body and the flat section of the container body cab be omitted. Accordingly, the medical container can be a general vial.

INDUSTRIAL APPLICABILITY

A medical instrument according to embodiments of the present invention covers at least a mouth section of a medical container having a tubular shape and including a container body with the mouth section at a distal end thereof and a soft sealing member that seals the mouth section includes: a cap including a first cap-side screw-engaged portion and a second cap-side screw-engaged portion, the first cap-side screw-engaged portion being formed of a cylindrical body and including a first screw portion formed in a spiral shape on an inner peripheral side of the cylindrical body around a center axis thereof and the second cap-side screw-engaged portion including a second screw portion formed in a spiral shape around the center axis on a more proximal-end side than the first cap-side screw-engaged portion on an outer peripheral side of the cylindrical body or on the inner peripheral side of the cylindrical body; an adapter including an adapter-side screw-engaged portion and a hollow needle that can penetrate the sealing member, the adapter-side screw-engaged portion being arranged movable in a proximal-end direction inside the cap and configured to be screw-engaged with the first cap-side screw-engaged portion; and a proximal-end side structure body including a proximal-end side screw-engaged portion to be screw-engaged with the second cap-side screw-engaged portion, a mounting section to be mounted on the container body so as to cover at least the mouth section, and a guide portion configured to guide the adapter along a moving direction and also restricts the adapter from rotating with the cap when the adapter moves in the proximal-end direction, wherein a pitch at the first screw portion is larger than a pitch at the second screw portion, and when screw-engagement between the second cap-side screw-engaged portion and the proximal-end side screw-engaged portion is released by rotating the cap around the center axis and the cap is detached from the proximal-end side structure body, the adapter moves in the proximal-end direction while being prevented from rotating by the guide portion, thereby allowing the adapter-side screw-engaged portion to be detached from the first cap-side screw-engaged portion, and further allowing the hollow needle to penetrate the sealing member so that inside of the container body communicates with outside via the hollow needle. Therefore, the medical container can be used immediately after detaching the cap.

Therefore, the medical instrument according to the present invention has industrial applicability.

What is claimed is:

1. A medical instrument configured to cover at least a mouth section of a medical container that includes a container body with the mouth section at a distal end and a sealing member that seals the mouth section, the medical instrument comprising:

a cap comprising a cylindrical body that includes:

a first cap-side screw-engaged portion that includes a first screw portion formed in a spiral shape around a center axis of the cylindrical body on an inner peripheral side of the cylindrical body, and a second cap-side screw-engaged portion that includes a second screw portion formed in a spiral shape around the center axis of the cylindrical body proximal of the first cap-side screw-engaged portion on an outer peripheral side of the cylindrical body or on the inner peripheral side of the cylindrical body;

an adapter comprising:

an adapter-side screw-engaged portion, and a hollow needle configured to penetrate the sealing member, the adapter-side screw-engaged portion being movable in a proximal-end direction inside the cap and configured to be screw-engaged with the first cap-side screw-engaged portion; and a proximal-end side structure body comprising:

a proximal-end side screw-engaged portion configured to be screw-engaged with the second cap-side screw-engaged portion, a mounting section configured to be mounted on the container body, and a guide portion configured to guide the adapter along a moving direction and to restrict the adapter from rotating together with the cap when the adapter moves in the proximal-end direction, wherein the medical device is configured such that, when screw-engagement between the second cap-side screw-engaged portion and the proximal-end side screw-engaged portion is released by rotating the cap around the center axis, the adapter moves in the proximal-end direction while being prevented from rotating by the guide portion, thereby allowing the adapter-side screw-engaged portion to be detached from the first cap-side screw-engaged portion, and further allowing the hollow needle to penetrate the sealing member so that an inside of the container body communicates with an outside via the hollow needle.

2. The medical instrument according to claim 1, wherein a pitch of the first screw portion is larger than a pitch of the second screw portion.

3. The medical instrument according to claim 1, wherein the mounting section is configured to be mounted on the container body so as to cover at least the mouth section.

4. The medical instrument according to claim 1, wherein a number of screw rotations of the first screw portion is less than or equal to a number of screw rotations of the second screw portion.

5. The medical instrument according to claim 1, wherein the proximal-end side structure body includes a housing section having a bottomed tubular shape and configured to house the container body on the proximal-end side of the proximal-end side screw-engaged portion.

6. The medical instrument according to claim 5, wherein the proximal-end side structure body includes:

a guide structure body in which the guide portion and the mounting section are integrated, and an outer cover member in which the housing section and the proximal-end side screw-engaged portion are integrated.

7. The medical instrument according to claim 6, wherein the medical instrument includes a rotation restricting unit configured to restrict the guide structure body from rotating with respect to the outer cover member.

8. The medical instrument according to claim 7, wherein rotation of the guide structure body with respect to the outer cover member is restricted by the rotation restricting unit, and the guide structure body is separable from the cap by rotating the cap around the center axis.

9. The medical instrument according to claim 8, wherein the cap includes:

a cap body, a ring portion that includes a rotation preventing portion configured to prevent the guide structure body from rotating with respect to the cap body, and a breakable portion disposed between the cap body and ring portion, wherein rotation of the ring portion with respect to the proximal-end side structure body is restricted by the rotation restricting unit, and wherein the breakable portion is configured such that a rotating force generated by rotating the cap around the center axis breaks the breaking portion to separate the cap body from the ring portion.

10. The medical instrument according to claim 9, wherein the second cap-side screw-engaged portion is formed on the outer peripheral side of the cap body and the ring portion.

11. The medical instrument according to claim 9, comprising a member that fixes the ring portion to the guide structure body.

12. The medical instrument according to claim 9, wherein the guide portion is formed of at least one elongated portion extending in a direction of the center axis and being separable into a distal-end side portion and a proximal-end side portion, and wherein the guide portion is configured such that, when the cap is detached, the distal-end side portion stays on the cap body side and the proximal-end side portion stays on the ring portion side.

13. The medical instrument according to claim 7, wherein the rotation restricting unit includes a restricting section formed on an inner peripheral portion of the housing section in a location different from where the proximal-end side screw-engaged portion is formed, the restricting section being configured to restrict the container body from rotating around the center axis.

14. The medical instrument according to claim 13, wherein the rotation restricting unit further includes a projected portion formed on an outer peripheral portion of the container body in a projecting manner, and an engagement portion formed on the mounting section and configured to be engaged with the projected portion.

15. The medical instrument according to claim 1, wherein the adapter includes a connector configured to communicate with the hollow needle and to be connected to a syringe while the cap is detached, and wherein the adapted is configured such that, when the syringe is connected to the connector, the syringe communicates with the container body via the connector and the hollow needle.

16. The medical instrument according to claim 1, wherein the second cap-side screw-engaged portion is on an outer peripheral side of the cylindrical body.

17. The medical instrument according to claim 1, wherein the cylindrical body of the cap includes a diameter-reduced section having a reduced inner diameter located distal of the first cap-side screw engaged portion.

18. The medical instrument according to claim 17, wherein cap further comprises an inner tube body fixed to the diameter-reduced section.

19. The medical instrument according to claim 1, further comprising the medical container.

20. A medical instrument configured to cover at least a mouth section of a medical container that includes a container body with the mouth section at a distal end and a sealing member that seals the mouth section, the medical instrument comprising:

a cap comprising a cylindrical body that includes:

means for first cap-side screw-engagement, and means for second cap-side screw-engagement;

an adapter comprising:

means for adapter-side screw-engagement, and means for penetrating the sealing member the means for adapter-side screw-engagement being movable in a proximal-end direction inside the cap and configured to be screw-engaged with the means for first cap-side screw-engagement; and a proximal-end side structure body comprising:

means for proximal-end side screw-engagement, means for mounting on the container body, and a means for guiding the adapter along a moving direction and for restricting the adapter from rotating together with the cap when the adapter moves in the proximal-end direction.

* * * * *